(12) United States Patent
Masson et al.

(10) Patent No.: US 12,347,553 B2
(45) Date of Patent: Jul. 1, 2025

(54) SYSTEM AND METHOD FOR MEDICAL PROCEDURE ROOM SET-UP OPTIMIZATION

(71) Applicant: EXPANDED EXISTENCE, INC., Windermere, FL (US)

(72) Inventors: Robert L. Masson, Windermere, FL (US); Raymond G. Oktavec, Fort Lauderdale, FL (US); Douglas Sonders, Ashburn, VA (US); Nicholas Cambata, Ashburn, VA (US)

(73) Assignee: EXPANDED EXISTENCE, INC., Windermere, FL (US)

( * ) Notice: Subject to any disclaimer, the term of this patent is extended or adjusted under 35 U.S.C. 154(b) by 0 days.

(21) Appl. No.: 18/768,169

(22) Filed: Jul. 10, 2024

(65) Prior Publication Data

US 2024/0363234 A1 Oct. 31, 2024

Related U.S. Application Data

(63) Continuation of application No. 17/567,236, filed on Jan. 3, 2022, now Pat. No. 12,094,599.
(Continued)

(51) Int. Cl.
*G16H 40/20* (2018.01)
*G06N 20/00* (2019.01)
*G16H 20/40* (2018.01)

(52) U.S. Cl.
CPC ............. *G16H 40/20* (2018.01); *G06N 20/00* (2019.01); *G16H 20/40* (2018.01)

(58) Field of Classification Search
CPC ........ G16H 40/20; G16H 20/40; G16H 40/63; G16H 40/67; G06N 20/00; G06N 3/084;
(Continued)

(56) References Cited

U.S. PATENT DOCUMENTS 8,452,615 B2  5/2013  Abri
9,129,054 B2  9/2015  Newana et al.
(Continued)

OTHER PUBLICATIONS

International Search Report and Written Opinion of the International Searching Authority issued on Apr. 12, 2022 in PCT/US2022/011358, filed Jan. 6, 2022.
(Continued)

*Primary Examiner* — Yuhui R Pan
(74) *Attorney, Agent, or Firm* — Sqagacity Legal PLLC

(57) ABSTRACT

A system for optimizing a medical procedure room initial set up includes a procedure room initial set up module configured to obtain at least one medical procedure room initial set up input and provide virtual image guidance based on the medical procedure room initial set up input. The system includes a procedure input module configured to acquire data in the medical procedure room initial set up and a machine learning module configured to analyze prestored data and compare the acquired data with the analyzed prestored data. The machine learning module is further configured to modify the at least one medical procedure room initial set up input based on the comparison and provide the modified at least one medical procedure room initial set up input to the procedure room initial set up module for optimizing the current medical procedure room initial set up.

18 Claims, 9 Drawing Sheets

Related U.S. Application Data

(60) Provisional application No. 63/199,562, filed on Jan. 8, 2021.

(58) Field of Classification Search
CPC .................. G06N 20/10; G06V 20/20; G06V 2201/034
See application file for complete search history.

(56) References Cited

U.S. PATENT DOCUMENTS

| | | |
|---|---|---|
| 10,176,642 B2 | 1/2019 | Tran et al. |
| 10,410,746 B2 | 9/2019 | Barrera et al. |
| 10,657,376 B2 * | 5/2020 | Lee et al. |
| 2017/0239000 A1 * | 8/2017 | Moctezuma De La Barrera ........ G16H 40/40 |
| 2018/0247023 A1 * | 8/2018 | Divine .................. G16H 20/40 |
| 2019/0005848 A1 | 1/2019 | Garcia Kilroy et al. |
| 2019/0080515 A1 | 3/2019 | Geri et al. |
| 2019/0307510 A1 | 10/2019 | Rotenberg et al. |
| 2020/0126661 A1 | 4/2020 | Flexman et al. |

OTHER PUBLICATIONS

International Preliminary Report on Patentability issued on Jul. 20, 2023 in PCT/US2022/011358, filed Jan. 6, 2022.

\* cited by examiner

SYSTEM AND METHOD FOR MEDICAL PROCEDURE ROOM SET-UP OPTIMIZATION

CROSS REFERENCE TO RELATED APPLICATIONS

The present application is a continuation of U.S. Non-Provisional application Ser. No. 17/567,236, filed Jan. 3, 2022, entitled "SYSTEM AND METHOD FOR MEDICAL PROCEDURE ROOM SET-UP OPTIMIZATION," which claims the benefit of U.S. Provisional Patent Application No. 63/199,562, filed Jan. 8, 2021, entitled "SYSTEM AND METHOD FOR MEDICAL PROCEDURE ROOM SET-UP OPTIMIZATION," which are incorporated by reference herein in their entirety.

BACKGROUND OF THE INVENTION

According to data from the National Center for Health Statistics, nearly fifty (50) million surgical inpatient procedures were performed in 2009 in the United States alone, and that number continues to grow. The setup of the medical procedure room is one of the most important factors for medical practitioner efficiency, patient safety, and team workflow. The setup and logistics of a medical procedure room should be optimized for efficiency and procedure predictability.

Before a medical procedure begins, the medical procedure room setup must be carefully planned. Additionally, proper medical procedure room setup also depends on the size, shape, and configuration of the medical procedure room. Thus, there is not a "one size fits all" approach to medical procedure room setup. Further, the medical procedure room must be equipped with an adequate number, and the right type, of supplies and tools, such as surgical instruments, lights, trays, robotic systems, anesthetic systems, scalpels and blades, and reusable and disposable supplies. Not only must the fixed or semi-fixed equipment be properly arranged prior to commencement of the procedure, but chargeable supplies (for example, sutures, sponges, clips, medical implants, screws, rods, arthroplasty devices, stimulators, needles, scalpel blades, catheters, drill bits) and disposable supplies (for example, gauze, gloves, liners, needles, syringes, and tubing) should be carefully tracked for billing and supply analysis and inventory management. During a medical procedure that demands the full attention of the medical practitioner and other medical personnel, the tracking of such equipment can easily be ignored or incorrectly logged.

Accordingly, medical procedure room setup and inventory management can be a complicated and time-consuming exercise that is prone to human error and failure to achieve user optimization.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
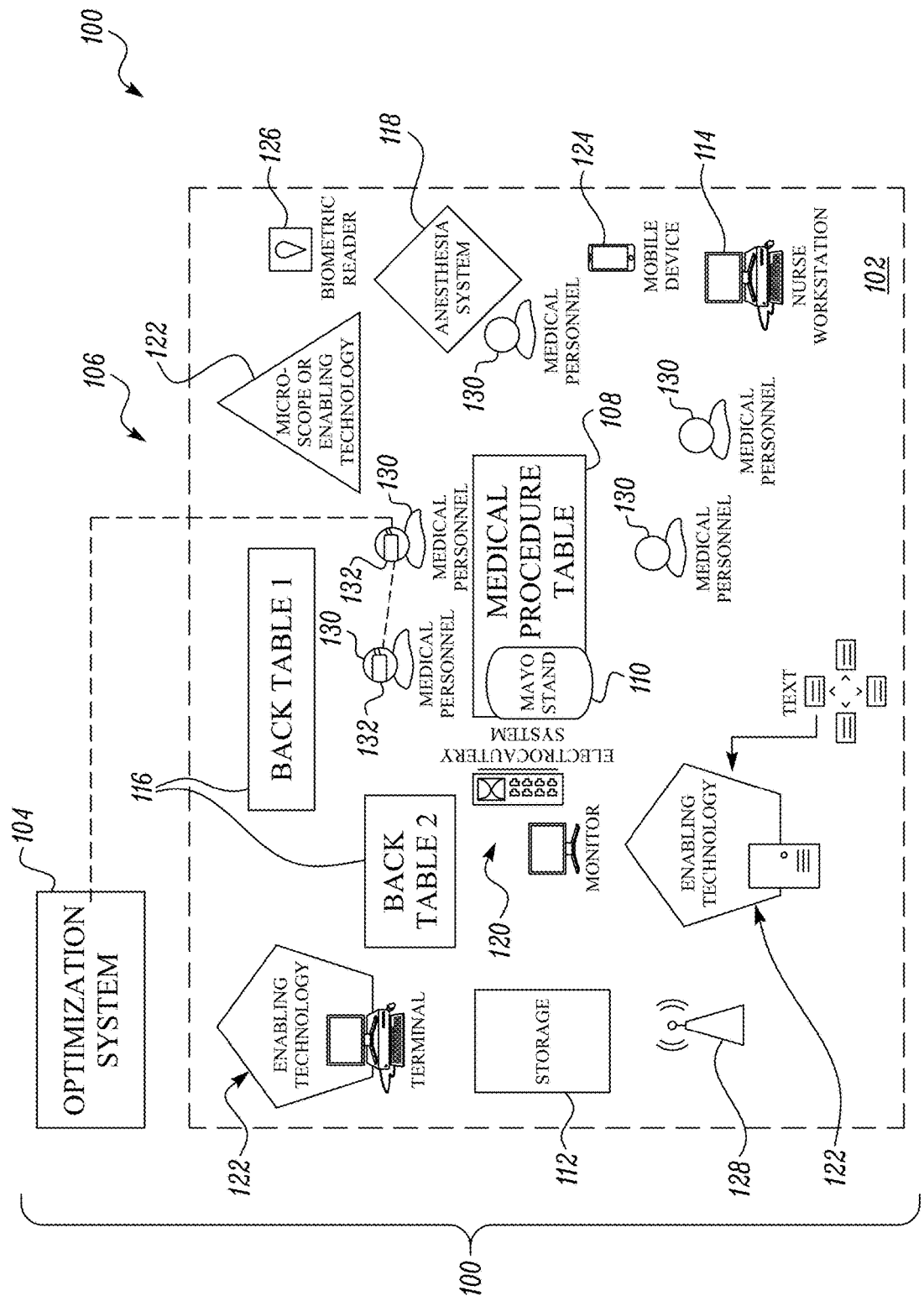
FIG. 1 is a block diagram of an exemplary medical procedure system in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In one aspect, a system for optimizing a medical procedure room initial set up is described. The system includes a procedure room initial set up module configured to obtain, from a storage device, at least one medical procedure room initial set up input associated with a medical practitioner identifier identifying a medical practitioner, a medical procedure identifier identifying a medical procedure to be performed, and a medical procedure room identifier identifying a medical procedure room for the medical procedure room initial set up and provide virtual image guidance, via one or more mixed reality devices, for the medical procedure room initial set up based on the received at least one medical procedure room initial set up input. The system further includes a procedure input module configured to acquire, via the one or more mixed reality devices, data associated with one or more of at least one item, at least one equipment, and at least one personnel in the medical procedure room initial set up. The system further includes a machine learning module configured to analyze prestored data associated with one or more of the at least one item, the at least one equipment, and the at least one personnel in one or more reference medical procedure room initial set ups corresponding to the medical practitioner identified by the medical practitioner identifier performing the medical procedure identified by the medical procedure identifier in the medical procedure room identified by the medical procedure room identifier and compare the acquired data associated with one or more of the at least one item, the at least one equipment, and the at least one personnel in the medical procedure room set up with the analyzed prestored data associated with one or more of the at least one item, the at least one equipment, and the at least one personnel in the one or more reference medical procedure room initial set ups. The machine learning module is further configured to modify the at least one medical procedure room initial set up input corresponding to the medical practitioner identifier, the medical procedure identifier, and the medical procedure room identifier for the medical procedure room initial set up based on the comparison and provide the modified at least one medical procedure room initial set up input to the procedure room initial set up module for optimizing the current medical procedure room initial set up. The machine learning module is further configured to identify, in the storage device, the modified at least one medical procedure room initial set up input as the at least one medical procedure room initial set up input.

In another aspect, a method for optimizing a medical procedure room set up is described. The method comprises obtaining, by a procedure room initial set up module, at least one medical procedure room initial set up input associated with a medical practitioner identifier identifying a medical practitioner, a medical procedure identifier identifying a medical procedure to be performed, and a medical procedure room identifier identifying a medical procedure room for the medical procedure room set up from a storage device and providing, by the procedure room initial set up module, virtual image guidance via one or more mixed reality devices, for the medical procedure room initial set up based on the received at least one medical procedure room initial set up input. The method further includes acquiring, by a procedure input module, data associated with one or more of at least one item, at least one equipment, and at least one personnel in the medical procedure room initial set up via the one or more mixed reality devices and analyzing, by a machine learning module, prestored data associated with one or more of the at least one item, the at least one equipment, and the at least one personnel in one or more reference medical procedure room initial set ups corresponding to the medical practitioner identified by the medical practitioner identifier performing the medical procedure identified by the medical procedure identifier in the medical procedure room identified by the medical procedure room identifier. Further, the method includes comparing, by the machine learning module, the acquired data associated with one or more of the at least one item, the at least one equipment, and the at least one personnel in the medical procedure room set up with the analyzed prestored data associated with one or more of the at least one item, the at least one equipment, and the at least one personnel in the one or more reference medical procedure room initial set ups and modifying, by the machine learning module, the at least one medical procedure room initial set up input corresponding to the medical practitioner identifier, the medical procedure identifier, and the medical procedure room identifier for the medical procedure room initial set up based on the comparison. Further, the method includes providing, by the machine learning module, the modified at least one medical procedure room initial set up input to the procedure room initial set up module for optimizing the current medical procedure room initial set up and identifying, by the machine learning module, the modified at least one medical procedure room initial set up input as the at least one medical procedure room initial set up input in the storage device.

Referring now to FIG. 1, a block diagram of an exemplary medical procedure system 100 is shown. In one embodiment, the medical procedure system 100 generally includes a medical procedure room 102 and an optimization system 104. The configuration of the medical procedure room 102 and/or optimization system 104, including physical placement of components, inventory and supplies, medical equipment used, medical personnel 130 involved, networking of equipment, and other characteristics may be referred to as a medical procedure room setup and is indicated in FIG. 1 with reference number 106. The medical procedure room 102 shown in FIG. 1 is a non-limiting example of a medical procedure system 100, and it will be understood that the systems and methods disclosed herein are not limited to the number, type, placement, and configuration of items of equipment, components, medical personnel 130, and/or other elements shown. Additionally, although shown within the medical procedure room 102 in FIG. 1, it will be understood that one or more of the items of equipment, components, medical personnel 130, and/or other elements of the medical procedure room setup 106 may be physically located outside or external to the walls of the room 102 and still be considered to be part of the medical procedure room setup 106.

Continuing to refer to FIG. 1, in one non-limiting example, the medical procedure room 102 may include a medical procedure table 108, one or more auxiliary tables or stands 110 (such as a Mayo stand), one or more storage closets or rooms 112, nurse workstations 114, back tables 116, anesthesia systems 118, electrocautery systems 120, enabling technology systems or workstations 122 (for example, but not limited to, microscopes, robotic surgical systems, networked robotics, illumination systems, or the like, and accompanying monitors or displays), user input devices 124 (such as mobile devices, tablets, or any communication device now known or in the future developed), biometric readers 126, and/or wireless transceivers 128, as well as medical personnel 130 (for example, but not limited to, surgical technicians, surgical team members (such as medical doctors and nurses), and anesthesiologists). In some embodiments, at least one member of medical personnel 130 wears a mixed reality device 132 during the medical procedure, and each mixed reality device 132 is in wireless and/or wired communication with the optimization system 104. As noted above, it will be understood that the medical procedure system 100 and medical procedure room setup 106 is not limited to those items shown in FIG. 1, and may include any number of items of equipment, electronic devices, imaging devices, surgical robots or other systems, lights, or any other devices and/or supplies preferred or required by the medical practitioner and/or other medical personnel 130.

Continuing to refer to FIG. 1, the exemplary medical procedure room setup 106 may be a preferred medical procedure room setup of the practitioner performing the medical procedure, based on the type of procedure, number of medical procedure room personnel, available room layout and dimensions, and other factors. As discussed in greater detail below, the layout of the preferred medical procedure room setup 106 may be uploaded or input into the optimization system 104 and may be displayed to a medical practitioner and/or medical personnel 130 through one or more mixed reality devices 132 of the optimization system 104. Further, in one embodiment, inventory of disposable items, chargeable items, and/or items that will remain in the patient is also uploaded or input into the optimization system 104 for tracking, analysis, and/or inventory management. In one embodiment, the optimization system 104 may suggest, or at least partially suggest, to the medical practitioner and/or medical personnel 130 an optimized medical procedure room setup 106, amount and type of inventory and items of medical equipment, and other characteristics to enhance efficiency of the medical procedure. For example, such suggestions may be based at least in part on user input and/or data collected by the optimization system 104 from previous medical procedures (hereinafter interchangeably referred to as reference medical procedures) of the same type or in the same medical procedure room. Additionally, or alternatively, each practitioner's preferred medical procedure room layout for each procedure may be stored in the optimization system 104 as a default setup and suggested to a user and/or the practitioner when planning a new setup for the same or similar medical procedure. As the medical practitioner, medical personnel 130, and/or other user of the optimization system 104 performs each step of the procedure and uses, moves, or removes each item of equipment and/or inventory, such activity is logged by the optimization system 104 for later analysis, inventory replenishment, education, procedural support, or other purposes.

Figure 2:
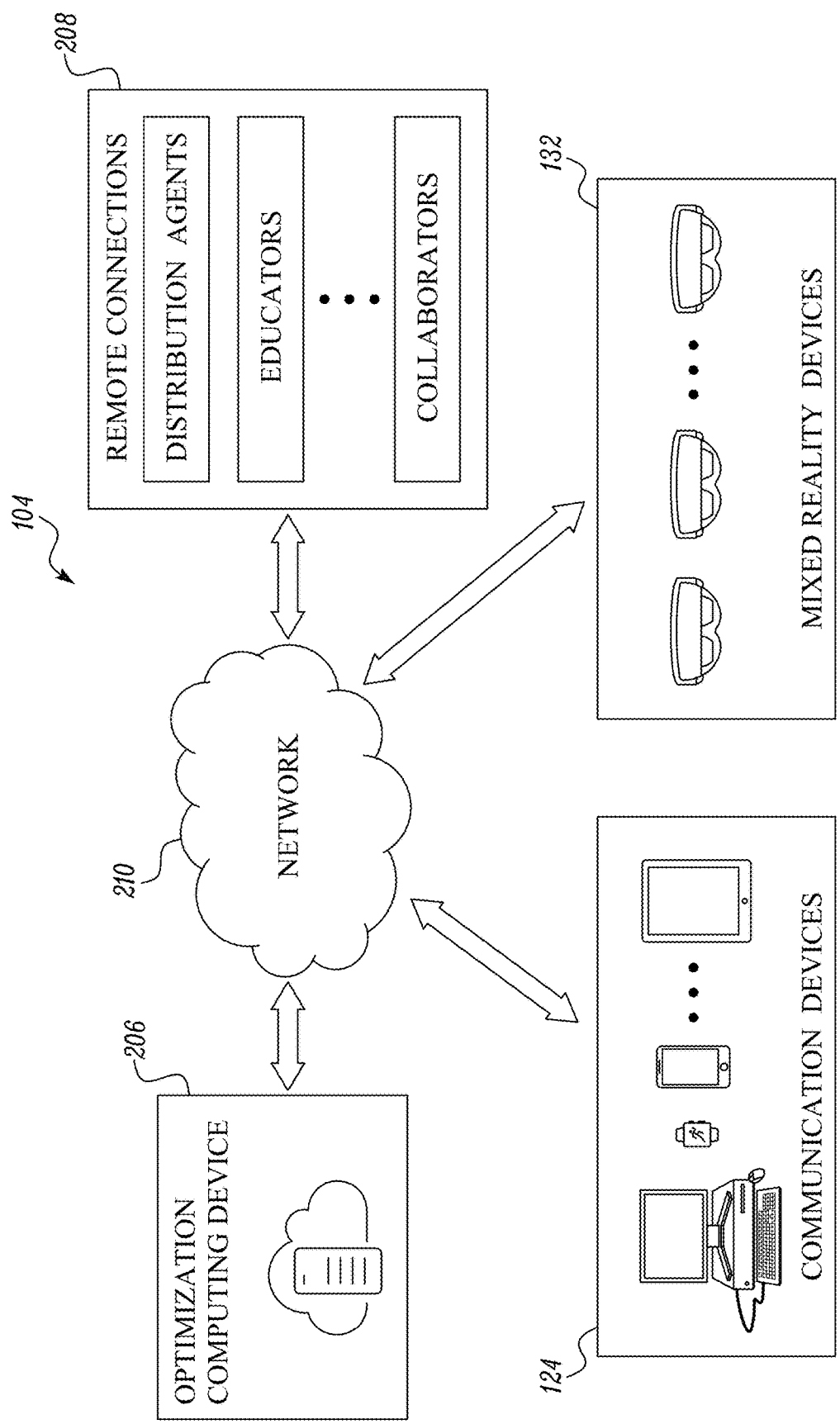
FIG. 2 is a block diagram of an optimization system in accordance with some embodiments.

FIG. 2 is a block diagram of an optimization system 104 in accordance with some embodiments. Specifically, the optimization system of FIG. 2 may be the optimization system 104 of FIG. 1. The optimization system 104 provides for medical practitioner specific room organization, set up, supply, logistics, tracking and performance across surgical and medical procedures with features for augmented reality, artificial intelligence and machine learning, as will be described further in accordance with some embodiments hereinbelow. As shown, the optimization system 104 includes one or more communication devices 124, one or more mixed reality devices 132, at least one optimization computing device 206, a network 210, and one or more remote connections 208.

The optimization computing device 206 may be communicatively coupled to, and receive information from, the one or more communication devices 124, the one or more mixed reality devices 132 and the one or more remote connections 208. Communication between the optimization computing device 206 and various components can occur through the network 210. In some embodiments, the network 210 is, for example, a wide area network (WAN) (for example, a transport control protocol/internet protocol (TCP/IP) based network), a cellular network, or a local area network (LAN) employing any of a variety of communications protocols as is well known in the art.

Figure 3:
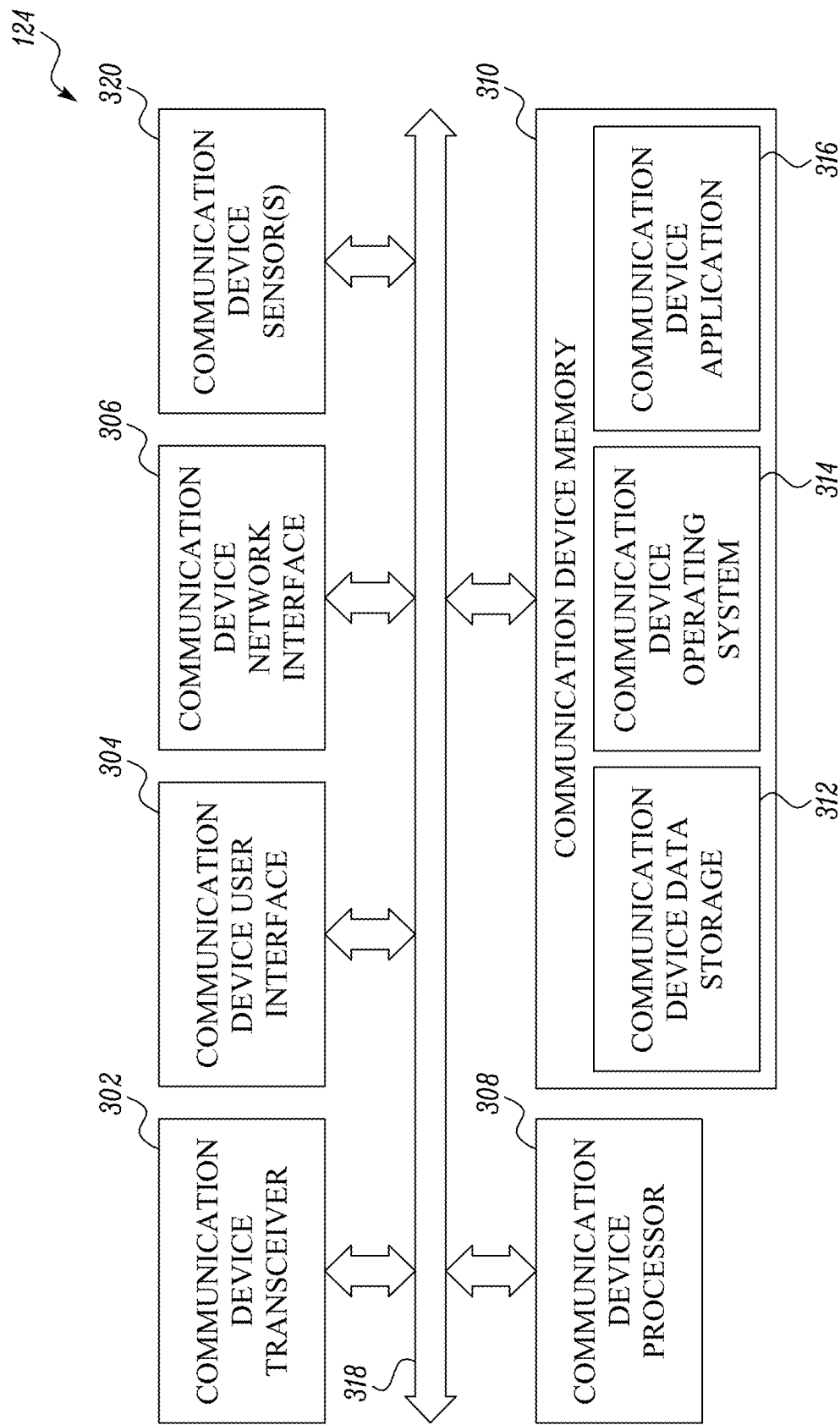
FIG. 3 is a block diagram of a communication device for use within the optimization system of FIG. 2 in accordance with some embodiments.

Each of the one or more communication devices 124 operates as a user interface for one or more medical procedure room personnel as will be further described with respect to FIG. 3.

Figure 4:
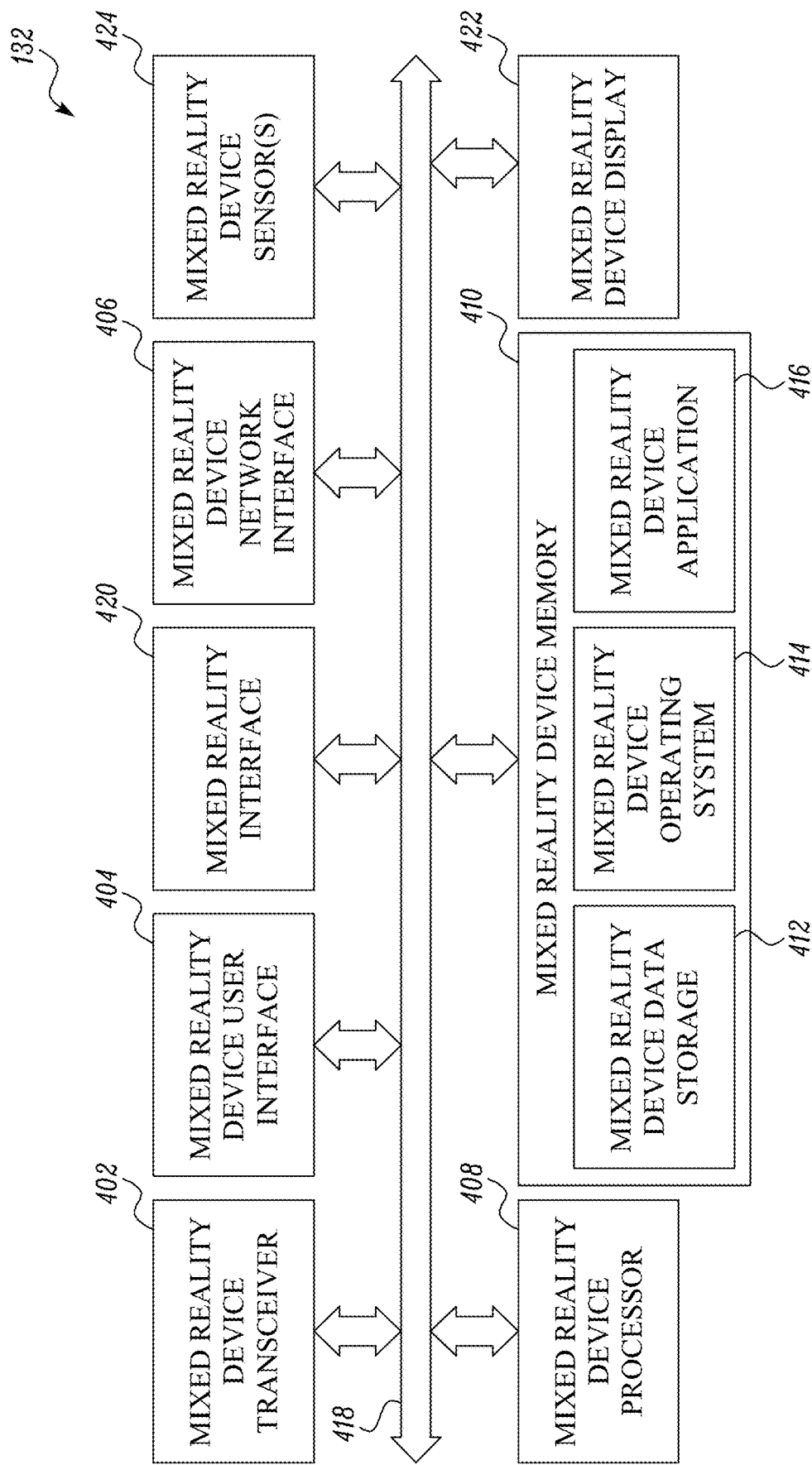
FIG. 4 is a block diagram of a mixed reality device for use within the optimization system of FIG. 2 in accordance with some embodiments.

Each of the one or more mixed reality devices 132 further operates as a user interface for one or more medical procedure room personnel as will be further described with respect to FIG. 4.

The one or more remote connections 208 interact with the optimization computing device 206 via the network 210 to receive and provide information external to the medical procedure room 102. The one or more remote connections 208 may be one or more distribution agents incorporated within the optimization system 104 or independently connected. The distribution agents may include, for example, but are not limited to, one or more of buyers, purchasing groups, pharmacies, anesthetic components, sterile processing departments (SPD), cleaning, storage, management, and/or any equivalent general processing department. The one or more remote connections 208 further may be one or more collaborators which may be technology collaborators or specialist collaborators and the like. The collaborators for example may include, but are not limited to, one or more of radiology, anesthesiology, fluoroscopy, electrophysiology, robotic and navigational systems, x-ray equipment techs, and the like. The one or more remote connections 208 may be one or more educators including, for example, but not limited to researchers, universities, training facilities, clinical trials, and the like.

In operation, the optimization computing device 206 optimizes the organization, preparation, and set up of a medical procedure space for efficient and predictable execution of one or more medical procedures. The optimization computing device 206, in some embodiments, operates to optimize pre-preparation of a procedure, orientation of medical personnel 130 for a procedure, and location and identification of equipment for a procedure.

FIG. 3 is a block diagram of one exemplary embodiment of a communication device 124 for use within the optimization system 104 of FIG. 2 in accordance with some embodiments. The communication device 124 is electrically and/or communicatively connected to a variety of other devices and databases as previously described with respect to FIG. 2 herein. In some embodiments, the communication device 124 includes a plurality of electrical and electronic components, providing power, operational control, communication, and the like within the communication device 124. For example, in one embodiment, the communication device 124 includes, among other things, a communication device transceiver 302, a communication device user interface 304, a communication device network interface 306, a communication device processor 308, a communication device memory 310, and one or more communication device sensors 320.

It should be appreciated by those of ordinary skill in the art that FIG. 3 depicts the communication device 124 in a simplified manner and a practical embodiment may include additional components and suitably configured logic to support known or conventional operating features that are not described in detail herein. It will further be appreciated by those of ordinary skill in the art that the communication device 124 may be a personal computer, desktop computer, tablet, smartphone, wearable device (wrist worn, eye worn, and the like), or any other computing device now known or in the future developed. It will further be appreciated by those of ordinary skill in the art that the communication device 124 alternatively may function within a remote server, cloud computing device, or any other remote computing mechanism now known or in the future developed.

The components of the communication device 124 (for example 302, 304, 306, 308, and 310) are communicatively coupled via a communication device local interface 318. The communication device local interface 318 may be, for example but not limited to, one or more buses or other wired or wireless connections, as is known in the art. The communication device local interface 318 may have additional elements, which are omitted for simplicity, such as controllers, buffers (caches), drivers, repeaters, and receivers, among many others, to enable communications. Further, the communication device local interface 318 may include address, control, and/or data connections to enable appropriate communications among the aforementioned components.

The communication device processor 308 is a hardware device for executing software instructions. The communication device processor 308 may be any custom made or commercially available processor, a central processing unit (CPU), an auxiliary processor among several processors associated with the communication device processor 308, a semiconductor-based microprocessor, or generally any device for executing software instructions. When the communication device 124 is in operation, the communication device processor 308 is configured to execute software stored within the communication device memory 310, to communicate data to and from the communication device memory 310, and to generally control operations of the communication device 124 pursuant to the software instructions.

The communication device user interface 304 may be used to receive user input from and/or for providing system output to the user or to one or more devices or components. User input may be provided via, for example, a keyboard, touch pad, and/or a mouse. System output may be provided via a display device, speakers, and/or a printer (not shown). The communication device user interface 304 may further include, for example, a serial port, a parallel port, an infrared (IR) interface, a universal serial bus (USB) interface and/or any other interface herein known or in the future developed.

The communication device network interface 306 may be used to enable the communication device 124 to communicate on a network, such as the network 210 of FIG. 2, a wireless access network (WAN), a radio frequency (RF) network, and the like. The communication device network interface 306 may include, for example, an Ethernet card or adapter or a wireless local area network (WLAN) card or adapter. Additionally, or alternatively the communication device network interface 306 may include a radio frequency interface for wide area communications such as Long-Term Evolution (LTE) networks, or any other network now known or in the future developed. The communication device network interface 306 may include address, control, and/or data connections to enable appropriate communications on the network.

The communication device memory 310 may include any non-transitory memory elements comprising one or more of volatile memory elements (for example, random access memory (RAM), nonvolatile memory elements (for example, read only memory "ROM"), and combinations thereof. Moreover, the communication device memory 310 may incorporate electronic, magnetic, optical, and/or other types of storage media. Note that the communication device memory 310 may have a distributed architecture, where various components are situated remotely from one another, but can be accessed by the communication device processor 308. The software in the communication device memory 310 may include one or more software programs, each of which includes an ordered listing of executable instructions for implementing logical functions. The software in the communication device memory 310 includes a suitable communication device operating system 314 and one or more communication device applications 316. The communication device operating system 314 controls the execution of other computer programs, such as the one or more communication device applications 316, and provides scheduling, input-output control, file and data management, memory management, and communication control and related services. The one or more communication device applications 316 may be configured to implement the various processes, algorithms, methods, techniques, and the like described herein.

The communication device memory 310 further includes a communication device data storage 312 used to store data. In the exemplary embodiment of FIG. 3, the communication device data storage 312 is located internal to the communication device memory 310 of the communication device 124. Additionally, or alternatively (not shown), the communication device data storage 312 may be located external to the communication device 124 such as, for example, an external hard drive connected to the communication device user interface 304. In a further embodiment (not shown), the communication device data storage 312 may be located external and connected to the communication device 124 through a network and accessed via the communication device network interface 306.

In operation, information for storage in the communication device data storage 312 may be entered via the communication device user interface 304. Alternatively, information for storage in the communication device data storage 312 may be received from the optimization computing device 206, the mixed reality devices 132, or the remote connections 208 via the communication device transceiver 302. Alternatively, information for storage in the communication device data storage 312 may be received from one or more sensors (not shown) external to the communication device 124 via the communication device transceiver 302. Alternatively, information for storage in the communication device data storage 312 may be received from one or more communication device sensors 320. For example, tutorials, room layouts, inventory, checklists, and the like may be stored in the communication device data storage 312. Medical personnel 130 can create, revise, or refine medical, procedure, and inventor notes as appropriate using the communication device user interface 304 to store new information in the communication device data storage 312.

The communication device 124 in the exemplary example includes the communication device transceiver 302. The communication device transceiver 302 incorporating within a communication device transceiver antenna (not shown), enables wireless communication from the communication device 124 to, for example, the optimization computing device 206 and the network 210 of FIG. 2. It will be appreciated by those of ordinary skill in the art that the communication device 124 may include a single communication device transceiver 302 as shown, or alternatively separate transmitting and receiving components, for example but not limited to, a transmitter, a transmitting antenna, a receiver, and a receiving antenna.

The communication device 124 in the illustrated example includes one or more communication device sensors 320. It will be appreciated by those of ordinary skill in the art that the one or more communication device sensors 320 may be of any sensor technology now known or in the future developed. For example, the one or more communication device sensors 320 may be IoT (Internet of Things) sensors, RFID (radio frequency identification) sensors, image sensors, light based (lidar) sensors, biometric sensors, printed sensors, wearable sensors, and optical image sensors. IoT sensors include temperature sensors, proximity sensors, pressure sensors, RF (radio frequency) sensors, pyroelectric IR (infrared) sensors, water-quality sensors, chemical sensors, smoke sensors, gas sensors, liquid-level sensors, automobile sensors and medical sensors.

Each of the one or more communication device sensors 320 comprise a detector allowing the monitoring and control of various parameters within the medical procedure room, for example, environmental parameters (temperature, humidity, carbon dioxide, and the like), technological processes (automation, robotics, materials analysis, and the like), and/or biometric tracking (movement, health contextual conditions, and the like). More specifically, the one or more communication device sensors 320 may provide personal fitness monitoring of a user of the communication device 124, a patient, and/or any other personnel associated with the medical procedure room. Alternatively, the one or more communication device sensors 320 may provide automation such as security, lighting, energy management, and access control for the medical procedure room. Alternatively, the one or more communication device sensors 320 may provide monitoring of the various devices and equipment associated with the medical procedure room. Alternatively, the one or more communication device sensors 320 may provide haptic or proprioception inputs, such as via accelerometers or bionic exoskeleton style components, which assess relative position of mechanical components of a joint or prosthesis or robotic arm, applicator device and the like. In operation, the one or more communication device sensors 320 communicate with one another, with other sensors within the medical procedure room, and/or with any other device within or external to the medical procedure room. For example, although not illustrated, the one or more communication device sensors 320 may communicate directly or indirectly with sensors implanted within a patient.

FIG. 4 is a block diagram of one exemplary embodiment of a mixed reality device 132 for use within the optimization system 104 of FIG. 2 in accordance with some embodiments. The mixed reality device 132 may provide a virtual reality interface in which a computer-simulated reality electronically replicates an environment with which a user may interact. In some embodiments, the mixed reality device 132 may provide an augmented reality interface in which a direct or indirect view of real-world environments in which the user is currently disposed are augmented (for example, supplemented, by additional computer-generated sensory input such as sound, video, images, graphics, Global Positioning System (GPS) data, or other information). In still other embodiments, the mixed reality device 132 may provide a mixed reality interface in which electronically generated objects are inserted in a direct or indirect view of real-world environments in a manner such that they may co-exist and interact in real time with the real-world environment and real-world objects. It will be appreciated by those of ordinary skill in the art that the mixed reality device 132 may comprise any mixed reality or virtual reality technology now known or in the future developed.

The mixed reality device 132 is electrically and/or communicatively connected to a variety of other devices and databases as previously described with respect to FIG. 2 herein. In some embodiments, the mixed reality device 132 includes a plurality of electrical and electronic components, providing power, operational control, communication, and the like within the mixed reality device 132. For example, the mixed reality device 132 in one embodiment includes, among other things, a mixed reality device transceiver 402, a mixed reality device user interface 404, a mixed reality device network interface 406, a mixed reality device processor 408, a mixed reality device memory 410, and one or more mixed reality device sensors 424.

It should be appreciated by those of ordinary skill in the art that FIG. 4 depicts the mixed reality device 132 in a simplified manner and a practical embodiment may include additional components and suitably configured logic to support known or conventional operating features that are not described in detail herein. It will further be appreciated by those of ordinary skill in the art that the mixed reality device 132 may be a head-mounted display device in the form of eyeglasses, goggles, a helmet, a visor, or any other mixed reality device eyewear now known or in the future developed. It will further be appreciated by those of ordinary skill in the art that the mixed reality device 132 generates and/or displays virtual reality images, mixed reality images, and/or augmented reality images. In the mixed reality device 132, a scene produced on a display device can be oriented or modified based on user input. The mixed reality device 132 provides a visual image in which real world and virtual world objects are presented together within a single display. It will be appreciated by those of ordinary skill in the art that although the embodiments herein are illustrated with a mixed reality device, alternative embodiments within the scope include a virtual reality device or an augmented reality device.

The components of the mixed reality device 132 (for example 402, 404, 406, 408 and 410) are communicatively coupled via a mixed reality device local interface 418. The mixed reality device local interface 418 may be, for example but not limited to, one or more buses or other wired or wireless connections, as is known in the art. The mixed reality device local interface 418 may have additional elements, which are omitted for simplicity, such as controllers, buffers (caches), drivers, repeaters, and receivers, among many others, to enable communications. Further, the mixed reality device local interface 418 may include address, control, and/or data connections to enable appropriate communications among the aforementioned components.

The mixed reality device processor 408 is a hardware device for executing software instructions. The mixed reality device processor 408 may be any custom made or commercially available processor, a central processing unit (CPU), an auxiliary processor among several processors associated with the mixed reality device processor 408, a semiconductor-based microprocessor, or generally any device for executing software instructions. When the mixed reality device 132 is in operation, the mixed reality device processor 408 is configured to execute software stored within the mixed reality device memory 410, to communicate data to and from the mixed reality device memory 410, and to generally control operations of the mixed reality device 132 pursuant to the software instructions.

The mixed reality device user interface 404 may be used to receive user input from and/or for providing system output to the user or to one or more devices or components. The mixed reality device user interface 404 may include one or more input devices, including but not limited to a navigation key, a function key, a microphone, a voice recognition component, joystick or any other mechanism capable of receiving an input from a user, or any combination thereof. Further, mixed reality device user interface 404 may include one or more output devices, including but not limited to a speaker, headphones, display, or any other mechanism capable of presenting an output to a user, or any combination thereof. In some embodiments, the mixed reality device user interface 404 includes a user interface mechanism such as a touch interface or gesture detection mechanism that allows a user to interact with the display elements of the mixed reality device display 422 or projected into the eyes of the user.

As illustrated, a mixed reality device display 422 may be a separate user interface or combined within the mixed reality device user interface 404. The mixed reality device display 422 may provide a two dimensional or three-dimensional image visible to the wearer of the mixed reality device 132. The mixed reality device display 422 may be, for example, a projection device for displaying information such as text, images, or video received from the optimization computing device 206, communication devices 124, and/or remote connections 208 via the network 210 of FIG. 2.

The mixed reality device user interface 404 may further include, for example, a serial port, a parallel port, an infrared (IR) interface, a universal serial bus (USB) interface and/or any other interface herein known or in the future developed.

The mixed reality device network interface 406 may be used to enable the mixed reality device 132 to communicate on a network, such as the network 210 of FIG. 2, a wireless access network (WAN), a radio frequency (RF) network, and the like. The mixed reality device network interface 406 may include, for example, an Ethernet card or adapter or a wireless local area network (WLAN) card or adapter. Additionally, or alternatively the mixed reality device network interface 406 may include a radio frequency interface for wide area communications such as Long-Term Evolution (LTE) networks, or any other network now known or in the future developed. The mixed reality device network interface 406 may include address, control, and/or data connections to enable appropriate communications on the network.

The mixed reality device memory 410 may include any non-transitory memory elements comprising one or more of volatile memory elements (for example, random access memory (RAM), nonvolatile memory elements (for example, read only memory "ROM"), and combinations thereof. Moreover, the mixed reality device memory 410 may incorporate electronic, magnetic, optical, and/or other types of storage media. Note that the mixed reality device memory 410 may have a distributed architecture, where various components are situated remotely from one another, but can be accessed by the mixed reality device processor 408. The software in the mixed reality device memory 410 may include one or more software programs, each of which includes an ordered listing of executable instructions for implementing logical functions. The software in the mixed reality device memory 410 includes a suitable mixed reality device operating system 414 and one or more mixed reality device applications 416. The mixed reality device operating system 414 controls the execution of other computer programs, such as the one or more mixed reality device applications 416, and provides scheduling, input-output control, file and data management, memory management, and communication control and related services. The one or more mixed reality device applications 416 may be configured to implement the various processes, algorithms, methods, techniques, and the like described herein.

The mixed reality device memory 410 further includes a mixed reality device data storage 412 used to store data. In the exemplary embodiment of FIG. 4, the mixed reality device data storage 412 is located internal to the mixed reality device memory 410 of the mixed reality device 132. Additionally, or alternatively, (not shown) the mixed reality device data storage 412 may be located external to the mixed reality device 132 such as, for example, an external hard drive connected to the mixed reality device user interface 404. In a further embodiment, (not shown) the mixed reality device data storage 412 may be located external and connected to the mixed reality device 132 through a network and accessed via the mixed reality device network interface 406.

In operation, information for storage in the mixed reality device data storage 412 may be entered via the mixed reality device user interface 404. In some embodiments, the mixed reality device data storage 412 stores data received by an augmented reality interface 420 which, for example, recognizes and registers the spatial characteristics of a medical procedure room.

Alternatively, information for storage in the mixed reality device data storage 412 may be received from the optimization computing device 206, the communication devices 124, or the remote connections 208 via the mixed reality device transceiver 402. Alternatively, information for storage in the mixed reality device data storage 412 may be received from one or more sensors (not shown) external to the mixed reality device 132 via the mixed reality device transceiver 402. Alternatively, information for storage in the mixed reality device data storage 412 may be received from one or more mixed reality device sensors 424. For example, tutorials, room layouts, inventory, checklists, and the like may be stored in the mixed reality device data storage 412. Medical personnel 130 can create, revise, or refine medical, procedure, and inventor notes as appropriate using the mixed reality device user interface 420 to store new information in the mixed reality device data storage 412.

The mixed reality device 132 in the exemplary example includes the mixed reality device transceiver 402. The mixed reality device transceiver 402 incorporating within a mixed reality device transceiver antenna (not shown), enables wireless communication from the mixed reality device 132 to, for example, the optimization computing device 206 and the network 210 of FIG. 2. It will be appreciated by those of ordinary skill in the art that the mixed reality device 132 may include a single communication device transceiver 302 as shown, or alternatively separate transmitting and receiving components, for example but not limited to, a transmitter, a transmitting antenna, a receiver, and a receiving antenna.

The mixed reality device 132 in the illustrated example includes one or more mixed reality device sensors 424. It will be appreciated by those of ordinary skill in the art that the one or more mixed reality device sensors 424 may be of any sensor technology now known or in the future developed. For example, the one or more mixed reality device sensors 424 may be IoT (Internet of Things) sensors, RFID (radio frequency identification) sensors, image sensors, light based (lidar) sensors, biometric sensors, printed sensors, wearable sensors, and optical image sensors. IoT sensors include temperature sensors, proximity sensors, pressure sensors, RF (radio frequency) sensors, pyroelectric IR (infrared) sensors, water-quality sensors, chemical sensors, smoke sensors, gas sensors, liquid-level sensors, automobile sensors and medical sensors.

Each of the one or more mixed reality device sensors 424 comprise a detector allowing the monitoring and control of various parameters within the medical procedure room, for example, environmental parameters (temperature, humidity, carbon dioxide, and the like), technological processes (automation, robotics, materials analysis, and the like), and/or biometric tracking (movement, health contextual conditions, and the like). More specifically, the one or more mixed reality device sensors 424 may provide personal fitness monitoring of a user of the mixed reality device 132, a patient, and/or any other personnel associated with the medical procedure room. Alternatively, the one or more mixed reality device sensors 424 may provide automation such as security, lighting, energy management, and access control for the medical procedure room. Alternatively, the one or more mixed reality device sensors 424 may provide monitoring of the various devices and equipment associated with the medical procedure room. Alternatively, the one or more mixed reality device sensors 424 may provide haptic or proprioception inputs, such as via accelerometers or bionic exoskeleton style components, which assess relative position of mechanical components of a joint or prosthesis or robotic arm, applicator device and the like. In operation, the one or more mixed reality device sensors 424 communicate with one another, with other sensors within the medical procedure room, and/or with any other device within or external to the medical procedure room.

Figure 5:
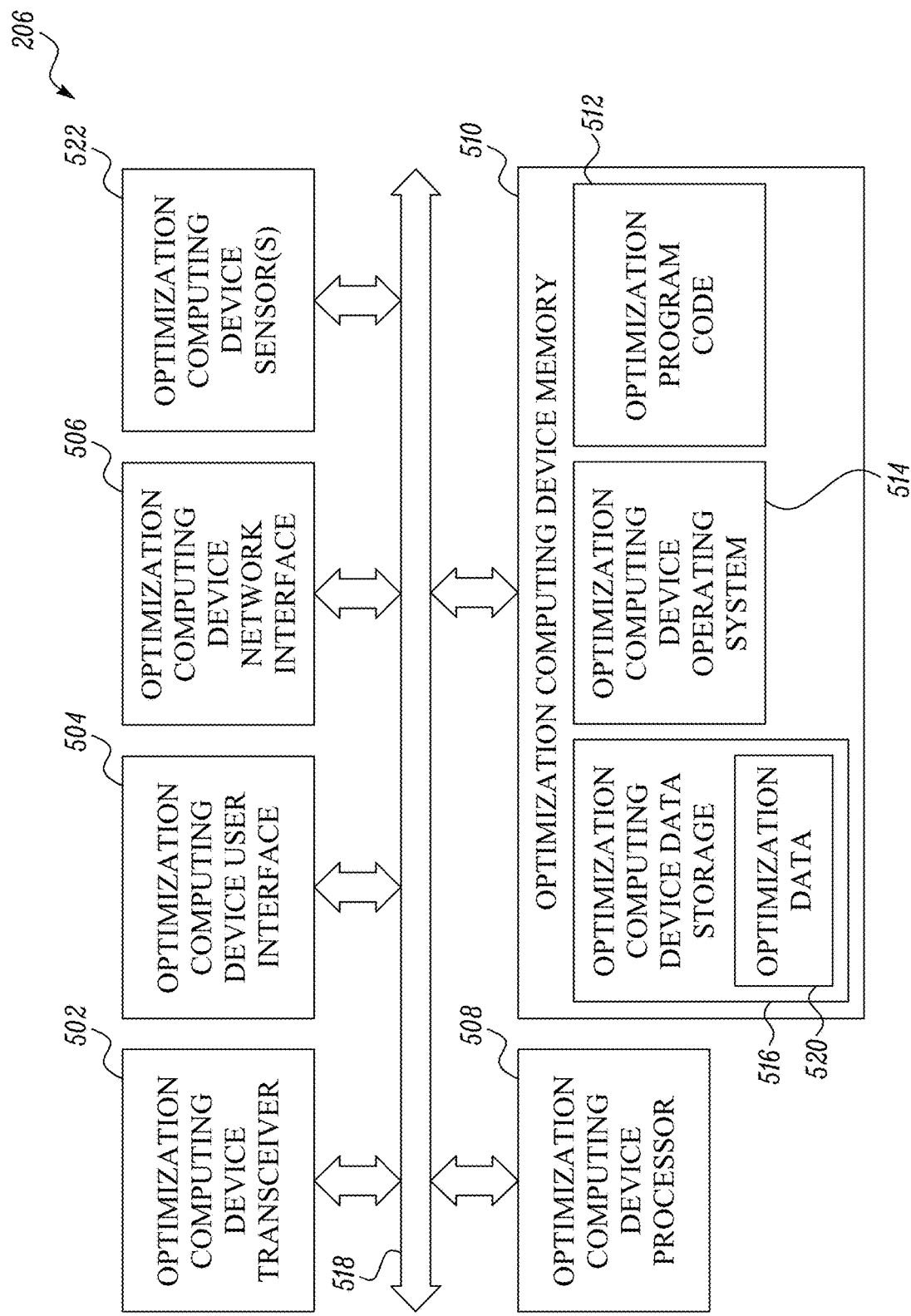
FIG. 5 is a block diagram of an optimization computing device for use within the optimization system of FIG. 2 in accordance with some embodiments.

FIG. 5 is a block diagram of one exemplary embodiment of an optimization computing device 206 for use within the optimization system 104 of FIG. 2. Specifically, the optimization computing device 206 can implement the various methods described herein.

The optimization computing device 206 is electrically and/or communicatively connected to a variety of other devices and databases as previously described with respect to FIG. 2 herein. In some embodiments, the optimization computing device 206 includes a plurality of electrical and electronic components, providing power, operational control, communication, and the like within the optimization computing device 206. For example, the optimization computing device 206 in one embodiment includes, among other things, an optimization computing device transceiver 502, an optimization computing device user interface 504, an optimization computing device network interface 506, an optimization computing device processor 508, an optimization computing device memory 510, and one or more optimization computing device sensor(s) 522.

It should be appreciated by those of ordinary skill in the art that FIG. 5 depicts the optimization computing device 206 in a simplified manner and a practical embodiment may include additional components and suitably configured logic to support known or conventional operating features that are not described in detail herein. It will further be appreciated by those of ordinary skill in the art that the optimization computing device 206 may be a personal computer, desktop computer, tablet, smartphone, or any other computing device now known or in the future developed.

It will further be appreciated by those of ordinary skill in the art that the optimization computing device 206 alternatively may function within a remote server, cloud computing device, or any other remote computing mechanism now known or in the future developed. For example, the optimization computing device 206 in some embodiments may be a cloud environment incorporating the operations of the optimization computing device processor 508, the optimization computing device memory 510, the optimization computing device user interface 504, and various other operating modules to serve as a software as a service model for the communication devices 124 and the mixed reality devices 132.

The components of the optimization computing device 206 (for example 502, 504, 506, 508 and 510) are communicatively coupled via an optimization computing device local interface 518. The optimization computing device local interface 518 may be, for example but not limited to, one or more buses or other wired or wireless connections, as is known in the art. The optimization computing device local interface 518 may have additional elements, which are omitted for simplicity, such as controllers, buffers (caches), drivers, repeaters, and receivers, among many others, to enable communications. Further, the optimization computing device local interface 518 may include address, control, and/or data connections to enable appropriate communications among the aforementioned components.

The optimization computing device processor 508 is a hardware device for executing software instructions. The optimization computing device processor 508 may be any custom made or commercially available processor, a central processing unit (CPU), an auxiliary processor among several processors associated with the optimization computing device processor 508, a semiconductor-based microprocessor, or generally any device for executing software instructions. When the optimization computing device 206 is in operation, the optimization computing device processor 508 is configured to execute software stored within the optimization computing device memory 510, to communicate data to and from the optimization computing device memory 510, and to generally control operations of the optimization computing device 206 pursuant to the software instructions.

The optimization computing device user interface 504 may be used to receive user input from and/or for providing system output to the user or to one or more devices or components. User input may be provided via, for example, a keyboard, touch pad, and/or a mouse. System output may be provided via a display device, speakers, and/or a printer (not shown). The optimization computing device user interface 504 may further include, for example, a serial port, a parallel port, an infrared (IR) interface, a universal serial bus (USB) interface and/or any other interface herein known or in the future developed.

The optimization computing device network interface 506 may be used to enable the optimization computing device 206 to communicate on a network, such as the network 210 of FIG. 2, a wireless access network (WAN), a radio frequency (RF) network, and the like. The optimization computing device network interface 506 may include, for example, an Ethernet card or adapter or a wireless local area network (WLAN) card or adapter. Additionally, or alternatively the optimization computing device network interface 506 may include a radio frequency interface for wide area communications such as Long-Term Evolution (LTE) networks, or any other network now known or in the future developed. The optimization computing device network interface 506 may include address, control, and/or data connections to enable appropriate communications on the network.

The optimization computing device memory 510 may include any non-transitory memory elements comprising one or more of volatile memory elements (for example random access memory (RAM), nonvolatile memory elements (for example, read only memory "ROM"), and combinations thereof. Moreover, the optimization computing device memory 510 may incorporate electronic, magnetic, optical, and/or other types of storage media. Note that the optimization computing device memory 510 may have a distributed architecture, where various components are situated remotely from one another, but can be accessed by the optimization computing device processor 508. The software in the optimization computing device memory 510 may include one or more software programs, each of which includes an ordered listing of executable instructions for implementing logical functions. The software in the optimization computing device memory 510 includes a suitable optimization computing device operating system 514 and optimization programming code 512. The optimization computing device operating system 514 controls the execution of other computer programs, such as the optimization program code 512, and provides scheduling, input-output control, file and data management, memory management, and communication control and related services. The optimization program code 512 may be configured to implement the various processes, algorithms, methods, techniques, and the like described herein.

The optimization computing device memory 510 further includes an optimization computing device data storage 516 used to store data. In the exemplary embodiment of FIG. 5, the optimization computing device data storage 516 is located internal to the optimization computing device memory 510 of the optimization computing device 206. Additionally, or alternatively, (not shown) the optimization computing device data storage 516 may be located external to the optimization computing device 206 such as, for example, an external hard drive connected to the optimization computing device user interface 504. In a further embodiment, (not shown) the optimization computing device data storage 516 may be located external and connected to the optimization computing device 206 through a network and accessed via the optimization computing device network interface 506.

The optimization computing device data storage 516, in accordance with some embodiments, stores optimization data 520 for operational use in the various processes, algorithms, methods, techniques, and the like described herein. In operation, information for storage in the optimization computing device data storage 516 may be entered via the optimization computing device user interface 504. Alternatively, information for storage in the optimization computing device data storage 516 may be received from the mixed reality devices 132, the communication devices 124, or the remote connections 208 via the optimization computing device transceiver 502. Alternatively, information for storage in the optimization computing device data storage 516 may be received from one or more sensors (not shown) external to the optimization computing device 206 via the optimization computing device transceiver 502. Alternatively, information for storage in the optimization computing device data storage 516 may be received from one or more optimization computing device sensors 522. For example, tutorials, room layouts, inventory, checklists, and the like may be stored in the optimization computing device data storage 516. Medical personnel 130 can create, revise, or refine medical, procedure, and inventor notes as appropriate using the optimization computing device user interface 504 to store new information in the optimization computing device data storage 516.

The optimization computing device 206 in the exemplary example includes the optimization computing device transceiver 502. The optimization computing device transceiver 502 incorporating within an optimization computing device transceiver antenna (not shown), enables wireless communication from the optimization computing device 206 to, for example, one or more communication devices 124, one or more mixed reality devices 132, and the network 210. It will be appreciated by those of ordinary skill in the art that the optimization computing device 206 may include a single optimization computing device transceiver as shown, or alternatively separate transmitting and receiving components, for example but not limited to, a transmitter, a transmitting antenna, a receiver, and a receiving antenna.

The optimization computing device 206 in the illustrated example includes one or more optimization computing device sensors 522. Each of the one or more optimization computing device sensors 522 comprise a detector allowing the monitoring and control of various parameters within the medical procedure room, for example, environmental parameters (temperature, humidity, carbon dioxide, and the like), technological processes (automation, robotics, materials analysis, and the like), and/or biometric tracking (movement, health contextual conditions, and the like). More specifically, the one or more optimization computing device sensors 522 may provide personal fitness monitoring of a user of the optimization computing device 206, a patient, and/or any other personnel associated with the medical procedure room. Alternatively, the one or more optimization computing device sensors 522 may provide automation such as security, lighting, energy management, and access control for the medical procedure room. Alternatively, the one or more optimization computing device sensors 522 may provide monitoring of the various devices and equipment associated with the medical procedure room. Alternatively, the one or more optimization computing device sensors 522 may provide haptic or proprioception inputs, such as via accelerometers or bionic exoskeleton style components, which assess relative position of mechanical components of a joint or prosthesis or robotic arm, applicator device and the like. In operation, the one or more optimization computing device sensors 522 communicate with one another, with other sensors within the medical procedure room, and/or with any other device within or external to the medical procedure room.

Figure 6:
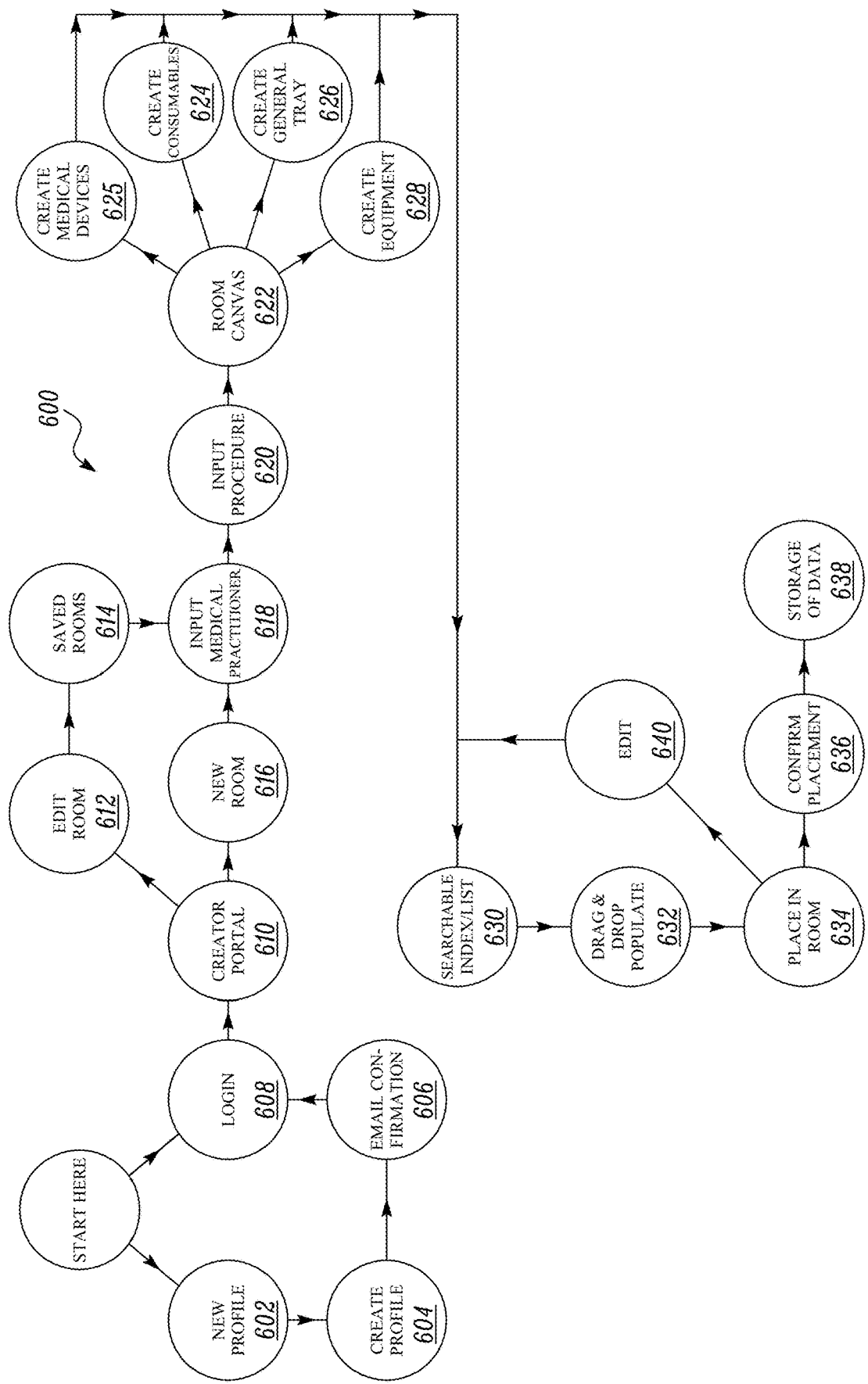
FIG. 6 is a flow diagram of a method for use in medical procedure room optimization in accordance with some embodiments.

FIG. 6 is a flow diagram of a method for medical procedure room optimization in accordance with some embodiments. Specifically, FIG. 6 is a flow diagram for an initial setup program 600 of a medical procedure room optimization in accordance with some embodiments. The initial setup program 600, for example, may be implemented within the optimization program code 512 of FIG. 5. In an alternative embodiment, the initial setup program 600 may be implemented as a cloud-based internet program accessed via the communication devices 124 and the optimization computing device 206. In yet another alternative embodiment, the initial setup program 600 can be distributively implemented within a system in which the various components are remotely located from each other in other embodiments. For example, a first set of components of the initial setup program 600 may be implemented and stored within the optimization computing device 206, a second set of components of the initial setup program 600 may be implemented and stored within one or more of the communication devices 124, a third set of components of the initial setup program 600 may be implemented and stored within one or more of the mixed reality devices 132, and/or a fourth set of components of the initial setup program 600 may be implemented and stored within other devices connected to the network 210 or otherwise communicatively coupled to the optimization computing device 206, the communication devices 124, and the mixed reality devices 132. It will be appreciated that any and all distribution arrangements of the initial setup program 600 are within the scope of the claimed invention herein.

It will be appreciated by those of ordinary skill in the art that the flow diagram of FIG. 6 is simply an exemplary embodiment and other alternative process flows are within the scope of the claimed invention herein.

In operation, the optimization computing device processor 508 accesses and executes the initial setup program 600. As illustrated in FIG. 6, the initial setup program 600 begins with the receipt of various inputs and information to process an initial medical procedure room setup. For example, the optimization computing device 206 receives user input at its optimization computing device user interface 504, stores the information within the user input in the optimization computing device data storage 516, and accesses the optimization program code 512 by the optimization computing device processor 508 for executing initial setup program 600. Alternatively, the communication device 124 receives user input including setup information at its communication device user interface 304, sends the information via its communication device network interface 306 through the network 210 to the optimization computing device 206. The optimization computing device 206 thereafter receives the information via its optimization computing device network interface 506, stores the information within the user input in the optimization computing device data storage 516, and accesses the optimization program code 512 by the optimization computing device processor 508 for executing initial setup program 600. It will be appreciated that the information may originate from and be received through various alternative methods in accordance with some embodiments.

Referring to FIG. 6, the initial setup program 600 begins generally with a new profile at operation 602 including creating a profile at operation 604 followed by email confirmation at operation 606. The initial setup program 600 thereafter proceeds to or alternatively begins with a login at operation 608. Next, in operation 610 a creator portal opens and displays. Next, in one embodiment, an edit to the medical procedure room occurs at operation 612. For example, the edit to the medical procedure room includes one or more of change in the available room layout and dimensions, change in position of the items corresponding to one or more of the medical devices, consumables, general tray, and equipment in the medical procedure room. Thereafter, the edited room is saved at operation 614. Alternatively, from operation 610, a new medical procedure room is created at operation 616. For instance, the new medical procedure room is created by providing required layout and dimensions for the new medical procedure room. It will be appreciated that the required layout and dimensions can be provided by using various techniques, such as but not limited to, uploading images of the medical procedure room. In some embodiments, the created new medical procedure room or the edited room is assigned a medical procedure room identifier. Thereafter, or after operation 614, the medical practitioner input is received and saved in operation 618. In accordance with various embodiments, the medical practitioner input may include the medical practitioner identifier, such as but not limited to, the name, the ID, or the like of the medical practitioner. Next, a procedure input is received and saved in operation 620. In accordance with various embodiments, the procedure input may include the procedure identifier, such as but not limited to, the name, the ID, or the like of the medical procedure. In operation 622 a room canvas is created. In accordance with various embodiments, the room canvas is created based on previous medical procedure room setups that are associated with the received medical practitioner input, the procedure input, and/or the edited/new medical room. The room canvas of operation 622 next includes creating consumables in operation 624, creating medical devices in operation 625, creating a general tray in operation 626, and creating equipment lists in operation 628.

It will be appreciated that in some embodiments, along with the information of room canvas created in 622, the data entered in operations 628, 624, 625, and 626 precisely configures a given medical practitioner's room organization for a given procedure. For example, the data entered in operations 628, 624, 625, and 626, in some embodiments, identifies inventory of fixed equipment, external enabling technologies such as microscopes, drills, fluoroscopy units, navigation systems, robotic systems, lights, electrophysiology systems, anesthetic systems, vacuum and gas management and operating room back table. Similarly, the data entered in operations 628, 624, 625, and 626, in some embodiments, identifies surgical instruments/items, reusable and disposable. For example, the data entered in operations 628, 624, 625, and 626, in some embodiments, identifies medical devices including pharmaceutical devices, implants, generators, stimulators, screws, plates, cages, arthroplasty joint replacement devices, heart valves, stents, coils, pacemakers, portals, biologics, catheters, and shunts. Similarly, the data entered in operations 628, 624, 625, and 626, in some embodiments, identifies chargeable resources/items such as sutures, sponges, clips, medical implants, screws, rods, arthroplasty devices, stimulators, needles, scalpel blades, and drill bits. Similarly, the data entered in operations 628, 624, 625, and 626, in some embodiments, identifies pharmaceutical resources such as medications, anesthetics, antibiotics, cardiac drugs, blood pressure drugs, sedatives, paralytic agents, pain management, and the like.

Continuing with FIG. 6, thereafter, in operation 630 all the items corresponding to the medical devices, consumables, general tray, and equipment's from the previous one or more operations, or the previous medical procedures are accessed from a searchable index/list in operation 630. For example, in some embodiments, preference cards for each medical practitioner's preferences and procedures are preloaded for access during the initial setup procedure 600.

Next, in operation 632, the items are populated in operation 632. For example, in one embodiment the items are populated using a drag and drop method. It will be appreciated that any suitable method can be used for operation 632. Next in operation 634, the items are placed in the medical procedure room 634 virtually. Thereafter, the placement is confirmed in operation 636 or alternatively, edits are completed in operation 640 and cycled back through operations 630, 632, and 634 until confirmation in operation 636 occurs.

Lastly, in operation 638, the room configuration, data and all other information associated with the medical practitioner for the particular procedure are stored. It will be appreciated, that the room configuration, data, and information may be stored within one or more of the optimization computing device memory 510, one or more of the communication device memory 310, one or more of the mixed reality device memory 410 or any combination thereof.

Upon completion of the initial setup program 600, the stored medical practitioner specific and procedure specific room configuration, data, and information would provide medical personnel 130 whose responsibility is to organize, prepare and set up a medical procedure space with specific detail to best organize, optimize and prepare the space for efficient and predictable execution of that procedure for that medical practitioner. It will be further appreciated that, in some embodiments, although not illustrated in FIG. 6, additional patient specific information may be entered and stored. It will further be appreciated that the initial setup created and stored can be used hereinafter to create a three-dimensional mixed reality map of the medical procedure room 102 with items, tools, consumables, and equipment placement based on medical practitioner and procedure preference.

Figure 7:
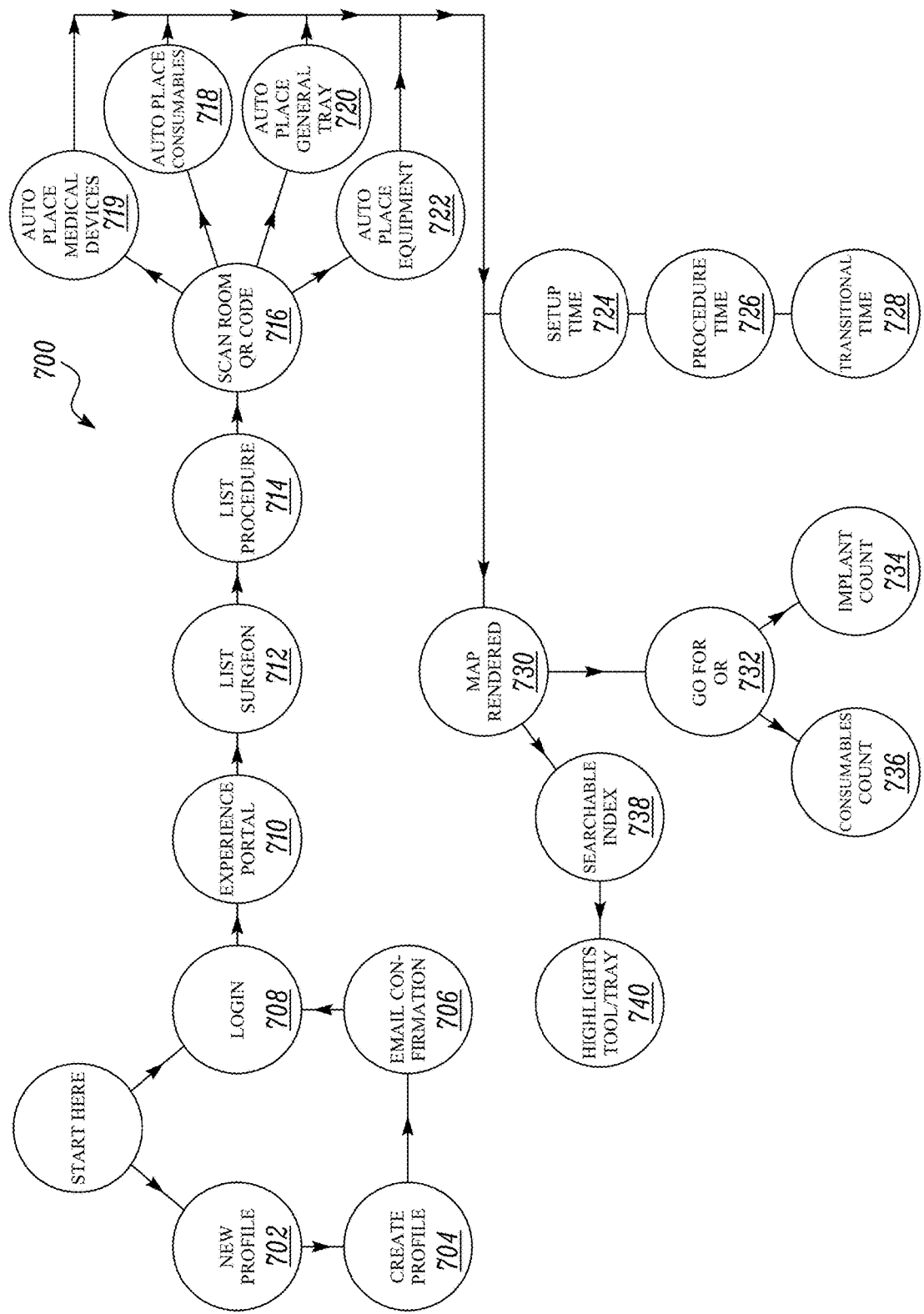
FIG. 7 is a flow diagram of a method of medical procedure room optimization in accordance with some embodiments.

FIG. 7 is a flow diagram of a method for medical procedure room optimization in accordance with some embodiments. Specifically, FIG. 7 is a flow diagram of a medical procedure room initial setup 700. The medical procedure room initial setup 700, for example, may be implemented within the mixed reality device applications 416 of FIG. 4. In an alternative embodiment, the medical procedure room initial setup 700 may be implemented as a cloud-based internet program accessed by one or more of the mixed reality devices 132. In yet another alternative embodiment, the medical procedure room initial setup 700 can be distributively implemented within a system in which the various components are remotely located from each other in other embodiments and accessed by one or more of the mixed reality devices 132. It will be appreciated that any and all distribution arrangements of the medical procedure room initial setup 700 are within the scope of the claimed invention herein.

It will be appreciated by those of ordinary skill in the art that the flow diagram of FIG. 7 is simply an exemplary embodiment and other alternative process flows are within the scope of the claimed invention herein.

In operation, the mixed reality device processor 408 accesses and executes the medical procedure room initial setup 700. As illustrated in FIG. 7, the medical procedure room initial setup 700 begins with the receipt of various inputs and information to process an initial medical procedure room setup 106. For example, the mixed reality device 132 receives user input at its mixed reality device user interface 404, stores the information within the user input in the mixed reality device data storage 412, and accesses the mixed reality device applications 416 by the mixed reality device processor 408 for executing the medical procedure room initial setup 700. Alternatively, the communication device 124 receives user input including setup information at its communication device user interface 304, sends the information via its communication device network interface 306 through the network 210 to the mixed reality device 132. The mixed reality device 132 thereafter receives the information via its mixed reality device network interface 406, stores the information within the user input in the mixed reality device data storage 412, and accesses the mixed reality device applications 416 by the mixed reality device processor 408 for executing the medical procedure room initial setup 700. It will be appreciated that the information may originate from and be received through various alternative methods in accordance with some embodiments.

Referring to FIG. 7, the medical procedure room initial setup 700 begins generally with a new profile at operation 702 including creating a profile at operation 704 followed by email confirmation at operation 706. The medical procedure room initial setup 700 thereafter proceeds to or alternatively begins with a login at operation 708. Next, in operation 710 an experience portal opens and displays. In some embodiments, the experience portal is displayed on the mixed reality device display 422, providing, for example, a mixed reality representation of the medical procedure room environment.

Next, in operation 712, a medical practitioner identifier (for example a medical practitioner) is selected from a list of medical practitioner identifiers. Next, in operation 714 a procedure identifier is selected from a list of procedure identifiers. Once the medical practitioner identifier and the procedure identifier have been selected, a medical procedure room 102 is identified. For example, in one embodiment the medical procedure room identifier is obtained by scanning a Quick Response code ("QR code" representing the medical procedure room 102 at operation 716.

With knowledge of the medical practitioner, the procedure, and the medical procedure room, the operation next auto places consumables in operation 718, auto places medical devices in operation 719, auto places the general tray in operation 720, auto places the equipment in 722, along with any auto placements related to the medical procedure room, procedure, and medical practitioner. It will be appreciated by those of ordinary skill in the art that any and all tangible items now known or later discovered for use in the particular procedure may be auto placed by the method 700. As previously described herein, the medical practitioner, procedure, and associated auto placements may be stored in one or more of the mixed reality device data storage 412, the communication device data storage 312, the optimization computing device data storage 516, a cloud-based memory accessed by one or more of the mixed reality devices 132, or any other associated memory communicatively coupled to the mixed reality device 132. In other words, representations in visual mixed reality format specific to a given medical practitioner for a given procedure may be stored in one or more data storage devices. In this manner, the medical procedure room initial setup 700 may provide preference cards for each medical practitioner's preferences and procedures pre-loaded for predictive planning and education on each procedure step by step from start to finish.

The medical procedure room initial setup 700 continues with operation 730 wherein a medical procedure room map is rendered. For example, the room map may be rendered on the mixed reality device display 422 for visual access. Thereafter, in operation 738 a searchable index is accessed, and lastly in operation 740 the tool/tray is highlighted. For example, in one embodiment, the inputted data would be mixed reality expressed by one or more of mixed reality interface augmented reality glasses/goggles/headpieces.

The previously described operations of the medical procedure room initial setup 700 is completed during a setup time 724. Further, a medical procedure 732 is completed during a procedure time 726, and lastly an implant count 734 and a consumable count 736 are identified and stored during a transitional time 728.

The medical procedure room initial setup 700 provides for configuration, organization and three-dimensional planning of the geometric space of the medical procedure room environment for a given medical practitioner for a given procedure. Specifically, the mixed reality device display, for example, a holograph glass system, may create a virtual three-dimensional environment for the entire operating organization field for a specific medical practitioner, and a specific procedure and for a specific patient, enabling complete data control and digitally managed integration of data of equipment for each specific procedure for each specific patient, with extreme precision of inventory use, control, management, performance, tracking and billing sales control and accuracy.

In one example, once the medical procedure room initial setup 700 is completed, a medical personnel 130, such as a surgical technician, would be able to look through the glasses (mixed reality device 132) and see mixed reality representation of each medical instrument, device or inventory item, and identify exactly where on the field it would be placed, what number of devices would be placed, what the device was called, and ultimately provide for instrument or device placement, identification, tracking registration and analytics, and ultimately inventory management. Disposable instruments or medical implants/devices would be able to be logged in for inventory at this step and converted to charge after application or use at the end of the procedure.

Figure 8:
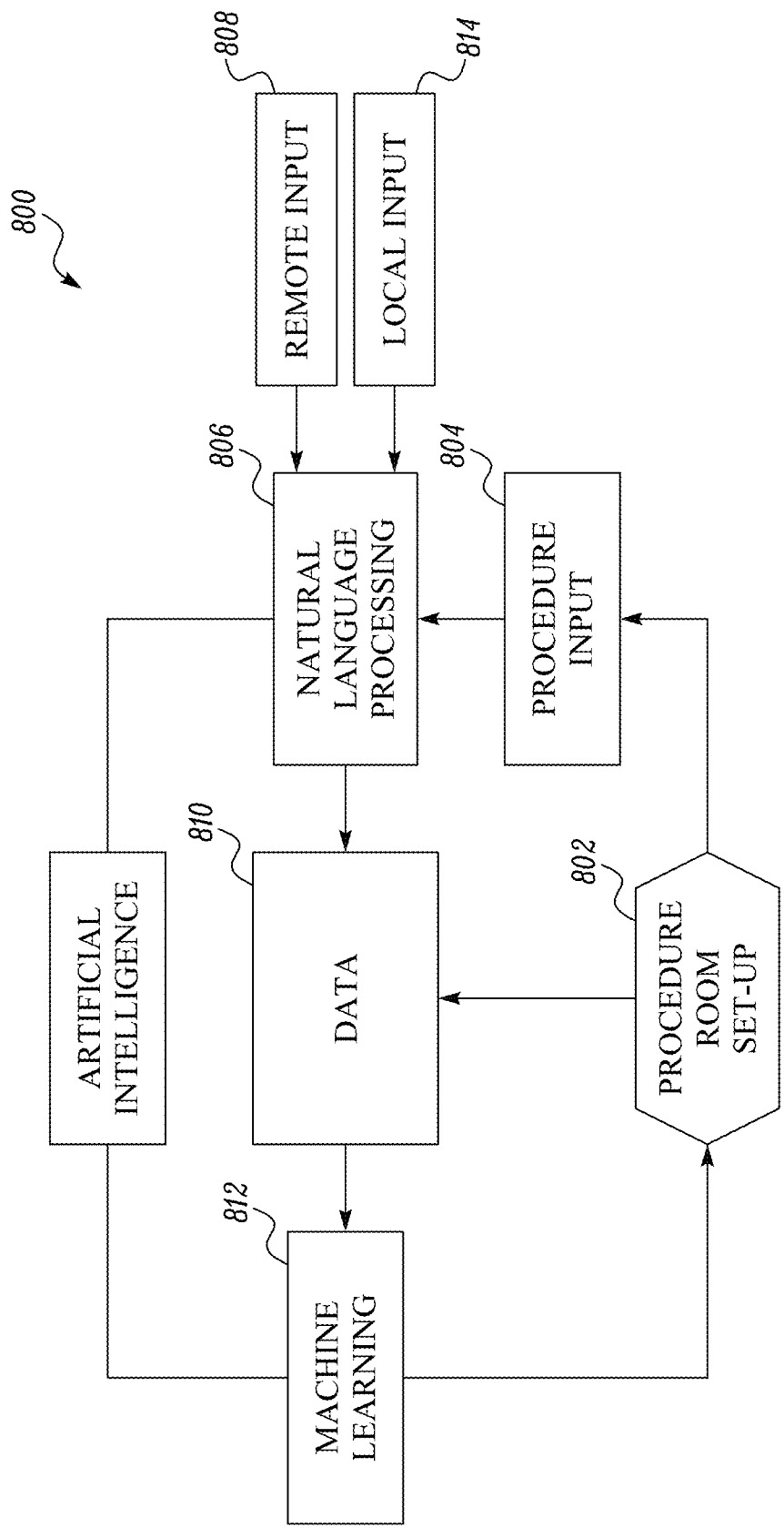
FIG. 8 is a functional block diagram of a medical procedure room set-up optimization system in accordance with some embodiments.

FIG. 8 is a functional block diagram of a system of medical procedure room set-up optimization in accordance with some embodiments. Specifically, FIG. 8 illustrates an optimization functional block diagram 800 utilizing artificial intelligence in a continuous loop system of optimization in accordance with some embodiments. The optimization functional block diagram 800, in some embodiments, may be implemented within the optimization system 104 as described previously herein. Specifically, the optimization functional block diagram 800, in some embodiments, illustrates the optimization of preparation of a procedure, orientation of medical personnel 130 for a procedure, and location and identification of equipment for a procedure. The real-time feedback and training of the optimization functional block diagram 800 allows for optimized efficiency and reduction of unnecessary steps throughout medical procedures.

Module 802 implements a medical procedure room set up 106. For example, in operation, the module 802 may implement the medical procedure room set up 106 as described hereinbefore for FIGS. 6 and 7. In some embodiments, the module 802 is configured to obtain a medical procedure room setup input associated with one or more of a medical practitioner identifier, a medical procedure identifier, and a medical procedure room identifier for the medical procedure room set up 106. The medical procedure room set up input may include one or more of count of disposable items required, count of chargeable items required, medical device required, primary equipment required, ancillary equipment required, medical personnel 130 required, geographical positioning of disposable item, geographical positioning of chargeable item, geographical positioning of medical device, geographical positioning of primary equipment, geographical positioning of ancillary equipment, geographical positioning of medical personnel 130, priority of use of disposable item, priority of use of chargeable item, priority of use of medical device, priority of use of primary equipment, priority of use of ancillary equipment, orientation of disposable item, orientation of chargeable item, orientation of medical device, orientation of primary equipment, orientation of ancillary equipment, and orientation of medical personnel 130. In some embodiments, the medical procedure room setup input may include one or more of the medical practitioner identifier, the medical procedure identifier, and the medical procedure room identifier.

In some embodiments, the procedure room set up of module 802 is implemented for a specific medical practitioner's preference for a particular procedure in a particular medical procedure room 102. For example, the data stored in the data module 810 may include pre-stored preference information for each medical practitioner's preferences and procedures. Medical personnel 130, in operation, utilize the medical practitioner specific, procedure specific, room specific data stored in the data module 810 to organize, prepare and set up a medical procedure space with specific detail to best organize, optimize and prepare the space for efficient and predictable execution of that procedure. For example, the procedure room setup may include a layout and orientation of where each medical practitioner and medical procedure room personnel will be positioned during the medical procedure. Information from the procedure room setup module 802 feeds into the data module 810 and also feeds into a procedure input module 804.

In some embodiments, the module 802 is configured to provide virtual image guidance, via one or more mixed reality devices 132, for the medical procedure room set up 106 based on the received medical procedure room setup input. In an embodiment, the virtual guidance is provided via a three-dimensional reality map reflecting the medical procedure room set up in accordance with the received input. For example, when the received medical procedure room setup input indicates the medical implants be placed on the back table 116, the module 802 is configured to provide virtual image guidance for example, a three-dimensional reality map representing the medical implants placed on the back table 116 for the medical procedure room setup 106. In some embodiments, when the medical procedure room setup input includes one or more of the medical practitioner identifier, the medical procedure identifier, and the medical procedure room identifier, the module 802 is configured to obtain previous medical procedure room setups associated with the respective one or more of the medical practitioner identifier, the medical procedure identifier, and the medical procedure room identifier and provide virtual image guidance corresponding the obtained previous medical procedure room set up. In operation, the procedure room set up of module 802 includes utilization of one or more mixed reality devices 132. The one or more mixed reality devices 132 provide the ability to use virtual image guidance for instrument and tray set up that will produce customizable three-dimensional templates for training other team members for optimal tray layout and lean principle set ups that reduce unnecessary time wasted. The one or more mixed reality devices 132 further may provide for instrument tray recognition and back table recognition for pre-planned procedure tray placement reducing setup times and turnover times between and during medical procedures. The one or more mixed reality devices 132 may also provide for instrument tray three-dimensional view of tray and expansion ability in order to picture virtual images of all instruments inside of tray without opening. In an embodiment, the instruments are Network Intelligent Operating Room Equipment having the ability for tracking, counting virtually through object recognition with names and purpose with detailed explanations. Tracking instruments in this way will provide less personnel training and provide a guide for limited passing throughout procedures. Using pre-populated lists stored in the data module 810 of exact instruments needed for each specific medical procedure and specific location provides for most efficient and lean practices. The one or more mixed reality devices 132 allows instrumentation to be viewed at all angles to become more familiar with functionality and how each tool works and assembles as well as dissembles.

The data stored in data module 810 may include, but is not limited to, medical procedure room organization, setup, logistics, performance, inventory and the like. Specifically, the data stored in data module 810 includes one or more of the data stored in the communication device data storage 312, the mixed reality device data storage 412, and the optimization data 520 stored in the optimization computing device data storage 516, all as described previously herein.

The data stored in the data module 810, may also include, for example, technique guides on instrumentation and various equipment used for each procedure preloaded for real-time feedback and training that will optimize efficiency and reduce unnecessary steps throughout procedures that will overall provide a safer environment to patient care. The data stored in the data module 810, may also include, for example, tutorial education for each instrument and each medical procedure tray by name and its purpose for use in medical procedure for real-time feedback, support or training. It will be appreciated that stored video tutorials for anatomy and physiology for a medical procedure will reduce time in training personnel for new procedures and cut down on redundancy and overall reduce risk factors and improve safety for patient care and healthcare providers. In general, the data stored in the data module 810 provides for predictive planning and education on each procedure step by step from start to finish. In an exemplary embodiment, the data module 810 is configured to store one or more of technique guides or tutorials associated with the medical procedure room set up.

The data stored in the data module 810, may also include, for example, guided imaging for setup of the various components of the medical procedure room 102 as described previously herein in FIG. 1 for continuous updating, editing, and ultimately optimizing. The data stored in the data module 810, may also include, for example, primary and ancillary supplies, primary and ancillary equipment listed specifically to each procedure. In accordance with various embodiments, the data module 810 is configured to store one or more previous medical procedure room setup (herein interchangeably referred to as reference medical procedure room setup) associated with one or more of the medical practitioner identifier, the medical procedure identifier, and the medical room identifier. For example, one or more medical procedure room setups previously used by a medical practitioner is associated with the medical practitioner identifier and stored in the data module 810. Similarly, one or more medical procedure room setups previously used for a medical procedure is associated with the medical procedure identifier and stored in the data module 810. Similarly, one or more medical procedure room setups previously used in a medical procedure room is associated with the medical room identifier and stored in the data module 810. In some embodiments, the one or more previous medical procedure room setups may be obtained from the tutorials and technique guides stored in the data module 810. The data stored in the data module 810 may provide medical personnel 130 with the ability to search for instruments to provide information for unfamiliar tools and give feedback of optimal placement. The data stored in the data module 810, may also include, for example, layout of equipment placement, relative to patients position for a medical procedure that will save on turnover times and efficiency for each procedure and practitioner preference. The layout and orientation may include where each of the medical practitioners and medical personnel 130 will be positioned during the procedure.

In operation, after the procedure room setup module 802, the optimization functional block diagram 800 proceeds to the procedure input module 804. The procedure input module 804 includes, but is not limited to, user input received by one or more of the communication device user interface 304, the communication device sensor(s) 320, the mixed reality device user interface 404, the mixed reality device sensor(s) 424, the optimization computing device user interface 504, and the optimization computing device sensor(s) 522. It will be appreciated by those of ordinary skill in the art that the user input may be received before, during, and after a particular medical procedure. In practice, the procedure input module 804 incorporates notes for each medical procedure, medical practitioner specific to each procedure for future efficiencies and personnel. The procedure input module 804 may also incorporate for example usage of one or more primary and ancillary devices and other medical items including disposable items. In one embodiment, these items include pre-bar code or reference code allowing to track disposable costs and reduce the amount of wasted procedure costs.

In practice, the procedure input module 804 is configured to acquire, via one or more mixed reality devices 132, data associated with one or more of item, equipment, and personnel in the medical procedure room set up 106. In an embodiment, the data associated with one or more of item, equipment, and personnel in the medical procedure room set up include one or more of identification, count, orientation, and geographical position of the respective item, equipment, and personnel in the medical procedure room. In operation, the one or more mixed reality devices 132 provide a view of the procedure room once the procedures starts so personnel will have an exact idea and view of where each member will be standing during the perioperative portion of the procedure. Further, the one or more mixed reality devices 132 may receive information about medical procedure resources in visual mixed reality format, including quantities and tracking of these resources, use, patterns for use, sequence of use, percentage and priority of use. In some embodiments, the one or more mixed reality devices 132 may receive information about quantity, movement, and/or orientation of the personnel in the medical procedure room set up.

In various embodiments, the procedure input module 804 is configured to transmit the received data to the machine learning module 812. The machine learning module 812 may be any system configured to learn and adapt itself to do better in changing environments. The machine learning module 812 may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing.

The machine learning module 812 may implement an iterative learning process. The learning may be based on a wide variety of learning rules or training algorithms. The learning rules may include one or more of back-propagation, patter-by-pattern learning, supervised learning, and/or interpolation. As a result of the learning, the machine learning module 812 may learn to determine the operations being performed by the optimization system 104.

Module 812 implements one or more machine learning algorithms to determine an optimal relationship of the data associated with the one or more of item, equipment, and personnel in the one or more reference medical procedure room setups with the one or more of the medical practitioner identifier, the medical procedure identifier, and the medical procedure room identifier. In accordance with some embodiments of the invention, the machine learning algorithm may utilize any machine learning methodology, now known or in the future developed, for classification. For example, the machine learning methodology utilized may be one or a combination of: Linear Classifiers (Logistic Regression, Naive Bayes Classifier); Nearest Neighbor; Support Vector Machines; Decision Trees; Boosted Trees; Random Forest; and/or Neural Networks. The machine learning module 812 continually evolves the specifics of a procedure room set-up in real time with new data inputs. The machine learning intent is to continually implement optimized procedure room set-ups overtime.

The machine learning module 812 is configured to analyze the prestored data, in the data module 810, associated with one or more of item, equipment, and personnel in one or more reference medical procedure room setups corresponding to the one or more of the medical practitioner identifier, the medical procedure identifier, and the medical procedure room identifier. For example, the prestored data associated with one or more of item, equipment, and personnel in the medical procedure room set up include one or more of count, orientation, and geographical position of the respective item, equipment, and personnel in the medical procedure room. In an embodiment, the analysis of the prestored data comprises determining the optimal relationship of the data associated with the one or more of item, equipment, and personnel in the one or more reference medical procedure room setups with the one or more of the medical practitioner identifier, the medical procedure identifier, and the medical procedure room identifier. For example, the machine learning module 812 analyzes the prestored data related to personnel in the medical procedure room in one or more reference medical procedure room setups and determines that, for example, the medical personnel 130 prefers to keep an auxiliary table 110 at the right side of the patient's bed while performing a surgery. The machine learning module 812 establishes this relationship between the auxiliary table 110 and the medical personnel identifier and stores the relationship data in the data module 810.

In various embodiments, the machine learning module 812 is configured to compare the acquired data associated with the one or more of item, equipment, and personnel in the medical procedure room set up with the analyzed pre-stored data associated with the respective one or more of item, equipment, and personnel in the one or more reference medical procedure room setups. In an embodiment, the machine learning module 812 is configured to compare the acquired data with the analyzed prestored data by determining whether the acquired data associated with the one or more of item, equipment, and personnel in the medical procedure room set up correspond to the determined optimal relationship for the one or more of the medical practitioner identifier, the medical procedure identifier, and the medical room identifier. In the example stated above, at this stage, the machine learning module 812 determines whether the auxiliary table 110 has been kept at the right side of the patient's bed, by comparing the data received from the one or more mixed reality devices 132 with the optimal relationship determined from the pre-stored data.

The machine learning module 812 is configured to provide recommendations to the module 802 for optimizing the medical procedure room set up based on the comparison. In accordance with various embodiments, the machine learning module 812 is configured to provide recommendations to the module 802 for optimizing the medical procedure room set up when the acquired data associated with the one or more of item, equipment, and personnel in the medical procedure room set up does not correspond to the determined optimal relationship. The machine learning module 812 is configured to provide the recommendations based on the determined optimal relationship. For example, as stated in the above example, at this stage when the auxiliary table 110 is not placed on the right side of the patient's bed then the machine learning module 812 will provide recommendations for correcting the position of the auxiliary table 110 by placing the auxiliary table 110 on the right side of the patient's bed. In an embodiment, the procedure room setup module 802 is further configured to update the virtual image guidance for the medical procedure room set up based on the received recommendations. In an embodiment, the machine learning module 812 is further configured to provide the at least one medical procedure room setup input corresponding to one or more of the medical practitioner identifier, the medical procedure identifier, and the medical procedure room identifier for the medical procedure room set up to the procedure room set up module 802.

In an embodiment, the machine learning module 812 is configured to compare the received input via the module 802 for the medical procedure room setup with the data acquired via the mixed reality devices 132, associated with the one or more of item, equipment, and personnel in the medical procedure room set up. In an embodiment, the machine learning module 812 is configured to generate an alert when the data associated with the one or more of item, equipment, and personnel in the medical procedure room set up is not consistent with the received the at least one medical procedure room setup input. In an exemplary embodiment, the machine learning module 812 is configured to generate warnings, prompts, alerts for counts, location, and management of missing instruments, devices, disposables on the field or within the patient as appropriate. For example, when the received input indicates that the medical implants are to be placed on the back table 116, the machine learning module 812 is configured to determine, based on the data acquired via the mixed reality devices 132, whether the medical implants are placed on the back table 116 in the medical procedure room setup and generate an alert when the medical implants are not placed on the back table 116 in the medical procedure room setup.

In an embodiment, the machine learning module 812 is configured to determine data associated with an item or an equipment required in the medical procedure room based on inputs received from the enabling technologies. In an embodiment, the input from the enabling technologies is received via one or more input module. For example, the input module may be a remote input module 808 and/or a local input module 814. The input from remotely present enabling technologies is received via the remote input module 808 and the input from locally present enabling technologies is received via the local input module 814. In an exemplary embodiment, the data associated with the item includes at least an identifier or a size of the respective item or equipment. For example, the machine learning module 812 may enable the medical procedure team, to measure and size medical instruments, implants and devices for patient specific use given the data available by enabling technologies such as operating microscope, fluoroscope, navigational system, robotic system, endoscopic system, for that medical practitioner, for that procedure. To this end, the machine learning module 812 determines whether the acquired data, via one or more mixed reality devices 132, associated with the one or more of item or equipment in the medical procedure room set up correspond to the determined data associated with the item or the equipment required in the medical procedure room. The machine learning module 812 is further configured to provide a recommendation to the procedure room setup module 802 to update the virtual image guidance for the medical procedure room set up to include the determined data associated with the item or the equipment, when the acquired data associated with the one or more of item or equipment in the medical procedure room set up is inconsistent with the determined data associated with the item or the equipment required in the medical procedure room.

In an embodiment, the one or more mixed reality devices 132 may provide for a data interface for managing gas, pharmaceutical and anesthetics quantity, dose, frequency, inventory, logistics and inventory ordering and replacement as linked to the external hospital-based management system on behalf of the specific patient In an embodiment, procedure inputs from the one or more mixed reality devices 132 may provide direct external visualization of the operating room environment through the eyes of the medical personnel 130 wearing the mixed reality device 132, through the external visualization of, for example, a microscope, an endoscopic system, a fluoroscopic system, a navigation/robotic system to an external expert, product specialist, or other professional. In some embodiments, a three-dimensional aerial perspective view of the medical procedure room 102 suite allows personnel capability for predictive planning of layout of equipment placement, relative to patients position for surgical case that will save on turnover times and efficiency for each surgical procedure and medical practitioner preference.

Further, in some embodiments, the one or more mixed reality devices 132 identifies whether one or more bed attachments are correct based on a right side or left side surgery (arm attachments and the like). Using a visual checklist, the one or more mixed reality devices 132 determines and provides procedure inputs that additional items for the medical practitioner are correct and documented as well as location is saved.

As described above, the input module may be the remote input module 808 and the local input module 814. It will further be appreciated by those of ordinary skill in the art that the remote input as illustrated by module 808, may also be received from remote connections 208 before, during, and after a particular medical procedure. Remote input of module 808, for example may include the integration of multimedia data management, acquisition and expression from secondary enabling medical technologies. In an embodiment, the local input as illustrated by the local input module 814 may be received from local enabling technologies present in the medical procedure room.

Module 806 implements a natural language processing algorithm. The natural language processing algorithm collects unstructured data from various sources including procedure input of module 804, remote inputs of module 808, and local inputs of module 814. These inputs are converted into machine-readable structured data, stored in the data module 810, and then analyzed by the machine learning module 812. It will be appreciated that the machine learning module 812, in some embodiments, may analyze the data in the data module 810 prior to a next procedure room set up of module 802, during a procedure itself to modify a procedure room set up, and/or after a procedure for analytical and training purposes. The machine learning module 812 may analyze the data in the data module 810 at other instances now known or hereinafter developed.

It will be appreciated that the optimization functional block diagram 800 in implementation provides for medical practitioner specific identification of the medical procedure room and the equipment and supply characteristics for any given procedure, and any given patient, enabling machine learning processes for optimization of procedure sequence, flow and execution, and ultimately help to define lean simple system design for optimal medical procedure room setup for that specific medical practitioner and for that specific procedure.

Figure 9:
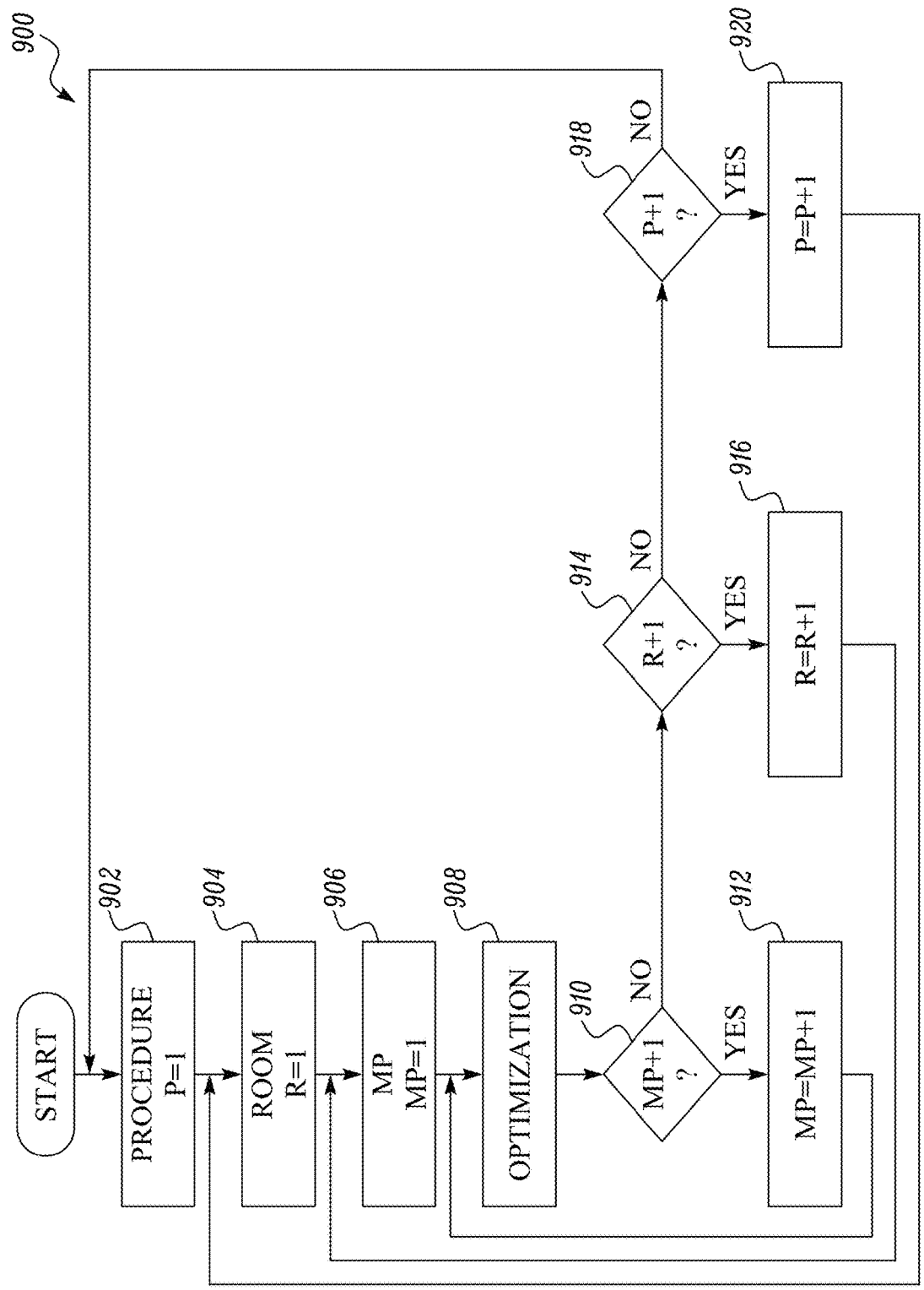
FIG. 9 is a flow diagram of a method of extended continuous optimization using the functionality of FIG. 8 in accordance with some embodiments.

FIG. 9 is a flow diagram of a method of extended continuous optimization using the functionality of FIG. 8 in accordance with some embodiments. Specifically, FIG. 9 is a flow diagram 900 illustrating the implementation of the optimization system 104 and various functionality as described previously herein for one or more medical practitioners, one or more medical procedure rooms, and/or one or more medical procedures.

The flow diagram 900 begins with operation 902 wherein a procedure identifier is initiated by setting the medical procedure identifier "P" equal to one "1". Next, in operation 904, a medical procedure room identifier is initiated by setting the medical procedure room identifier "R" equal to one "1". Next, in operation 906, a medical practitioner identifier is initiated by setting the medical practitioner identifier "MP" equal to one "1".

Next, in operation 908, optimization functionality occurs. It will be appreciated by those of ordinary skill in the art that the optimization operation 908 includes the optimization described previously herein for FIGS. 1 through 8. After the optimization operation 908, the process of flow diagram 900 continues to operation 910 in which it is determined whether there are more medical practitioners. Specifically, it is determined whether MP=MP+1 is to be included. When MP+1 is determined to be included, the process continues to operation 912 in which the MP identifier is incremented to MP=MP+1. The process then cycles back to the optimization operation 908. In operation, at this stage, the optimization system 104 is configured to optimize the medical procedure room set up based on the plurality of received medical practitioner identifiers (in other words, MP and MP+1). For example, the optimization system 104 is configured to obtain the preferred medical procedure room setup associated with the received medical practitioner identifiers and optimize the medical procedure room set up based on the preferred medical procedure room setup associated with the received medical practitioner identifiers. In some embodiments, the optimization may include merging the preferred medical procedure room setup associated with the received plurality of medical practitioner identifiers or selecting the preferred medical procedure room setup associated with the primary/predefined medical practitioner, in case of any conflict. The optimized medical procedure room setup may then be associated with the received plurality of medical practitioner identifiers and stored in the data module 810. When, in operation 910, it is determined that there is no MP+1 to include, the process continues to operation 914 in which it is determined whether there are more medical procedure rooms. Specifically, it is determined whether R=R+1 is to be included. When R+1 is determined to be included, the process continues to operation 916 in which the R identifier is incremented to R=R+1. The process then cycles back to the operation 906. In operation, at this stage, the optimization system 104 is configured to optimize the medical procedure room set up based on the plurality of received medical procedure room identifiers (for example, R and R+1). For example, the optimization system 104 is configured to obtain the preferred medical procedure room setups associated with the received medical procedure room identifiers and optimize the medical procedure room set up based on the preferred medical procedure room setups associated with the received medical procedure room identifiers. The optimized medical procedure room setup may then be associated with the received plurality of medical procedure room identifiers and stored in the data module 810.

When, in operation 914, it is determined that there is no R+1 to include, the process continues to operation 918 in which it is determined whether there are more medical procedures. Specifically, it is determined whether P=P+1 is to be included. When P+1 is determined to be included, the process continues to operation 920 in which the P identifier is incremented to P=P+1. The process then cycles back to the operation 904. In operation, at this stage, the optimization system 104 is configured to optimize the medical procedure room set up based on the plurality of received medical procedure identifiers (for example, P and P+1). For example, the optimization system 104 is configured to obtain the preferred medical procedure room setups associated with the received medical procedure identifiers and optimize the medical procedure room set up based on the preferred medical procedure room setups associated with the received medical procedure identifiers. The optimized medical procedure room setup may then be associated with the received plurality of medical procedure identifiers and stored in the data module 810.

When, in operation 918, it is determined that there is no P+1 to include, the process cycles back to operation 902 in which P is reset. In this manner, the optimization system 104 and methods described herein provide continuous optimization for one or more medical practitioners, one or more medical procedure rooms, and one or more medical procedures and any combination therein.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element preceded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A system for optimizing a medical procedure room initial set up, the system comprising:
   a procedure room initial set up module configured to:
      obtain, from a storage device, at least one medical procedure room initial set up input associated with a medical practitioner identifier identifying a medical practitioner, a medical procedure identifier identifying a medical procedure to be performed, and a medical procedure room identifier identifying a medical procedure room for the medical procedure room initial set up, and
      provide virtual image guidance, via one or more mixed reality devices, for the medical procedure room initial set up based on the received at least one medical procedure room initial set up input;
   a procedure input module configured to:
      acquire, via the one or more mixed reality devices, data associated with one or more of at least one item, at least one equipment, and at least one personnel in the medical procedure room initial set up; and
   a machine learning module configured to:
      analyze prestored data associated with one or more of the at least one item, the at least one equipment, and the at least one personnel in one or more reference medical procedure room initial set ups corresponding to the medical practitioner identified by the medical practitioner identifier performing the medical procedure identified by the medical procedure identifier in the medical procedure room identified by the medical procedure room identifier,
      compare the acquired data associated with one or more of the at least one item, the at least one equipment, and the at least one personnel in the medical procedure room set up with the analyzed prestored data associated with one or more of the at least one item, the at least one equipment, and the at least one personnel in the one or more reference medical procedure room initial set ups, modify the at least one medical procedure room initial set up input corresponding to the medical practitioner identifier, the medical procedure identifier, and the medical procedure room identifier for the medical procedure room initial set up based on the comparison, provide the modified at least one medical procedure room initial set up input to the procedure room initial set up module for optimizing the current medical procedure room initial set up, and identify, in the storage device, the modified at least one medical procedure room initial set up input as the at least one medical procedure room initial set up input; and an input module configured to:
receive inputs from one or more medical enabling technologies;

wherein the machine learning module is further configured to:

determine data associated with an item or an equipment required in the medical procedure room based on the received inputs, wherein the data includes at least an identifier or a size of the respective item or equipment, determine whether the acquired data associated with one or more of the item or the equipment in the medical procedure room initial set up correspond to the determined data associated with the item or the equipment required in the medical procedure room, and provide a recommendation to the procedure room initial set up module to update the virtual image guidance for the medical procedure room set up to include the determined data associated with the item or the equipment, when the acquired data associated with one or more of the item or the equipment in the medical procedure room initial set up is inconsistent with the determined data associated with the item or the equipment required in the medical procedure room.

2. The system of claim 1, wherein the machine learning module is further configured to:

compare the received at least one medical procedure room initial set up input with the acquired data associated with one or more of the at least one item, the at least one equipment, and the at least one personnel in the medical procedure room initial set up, and generate an alert when the acquired data associated with one or more of the at least one item, the at least one equipment, and at least one personnel in the medical procedure room set up is inconsistent with the received the at least one medical procedure room initial set up input.

3. The system of claim 1, wherein the analyzing further comprises determining an optimal relationship of the data associated with one or more of the at least one item, the at least one equipment, and the at least one personnel in the one or more reference medical procedure room initial set ups with the medical practitioner identifier, the medical procedure identifier, and the medical procedure room identifier, and further wherein the comparing comprises determining whether the acquired data associated with one or more of the at least one item, the at least one equipment, and the at least one personnel in the medical procedure room initial set up correspond to the determined optimal relationship for the medical practitioner identifier, the medical procedure identifier, and the medical room identifier.

4. The system of claim 3, wherein the machine learning module is configured to implement one or more machine learning algorithms to determine the optimal relationship of the data associated with one or more of the at least one item, the at least one equipment, and the at least one personnel in the one or more reference medical procedure room initial set ups with the medical practitioner identifier, the medical procedure identifier, and the medical procedure room identifier.

5. The system of claim 1, wherein the machine learning module is configured to provide recommendations to the procedure room initial set up module for optimizing the medical procedure room initial set up based on the comparison and further wherein the procedure room set up module is further configured to update the virtual image guidance for the medical procedure room initial set up based on the received recommendation.

6. The system of claim 1, wherein the medical procedure room initial set up input includes one or more of a count of at least one disposable item required, a count of at least one chargeable item required, a count of at least one medical device required, a count of at least one primary equipment required, a count of at least one ancillary equipment required, a count of at least one medical personnel required, a geographical positioning of at least one disposable item, a geographical positioning of at least one chargeable item, a geographical positioning of at least one medical device, a geographical positioning of at least one primary equipment, a geographical positioning of at least one ancillary equipment, a geographical positioning of at least one medical personnel, a priority of use of at least one disposable item, a priority of use of at least one chargeable item, a priority of use of at least one medical device, a priority of use of at least one primary equipment, a priority of use of at least one ancillary equipment, an orientation of at least one disposable item, an orientation of at least one chargeable item, an orientation of at least one medical device, an orientation of at least one primary equipment, an orientation of at least one ancillary equipment, and an orientation of at least one medical personnel.

7. The system of claim 1, wherein the data associated with one or more of the at least one item, the at least one equipment, and the at least one personnel in the medical procedure room initial set up include one or more of an orientation and a geographical position of one or more of the at least one item, the at least one equipment, and the at least one personnel in the medical procedure room.

8. The system of claim 1, wherein the data associated with one or more of the at least one item, the at least one equipment, and the at least one personnel in the medical procedure room initial set up include a count of one or more of the at least one item, the at least one equipment, and the at least one personnel in the medical procedure room.

9. The system of claim 1, further comprising:

a data module configured to store one or more of technique guides or tutorials associated with the medical procedure room initial set up, wherein the procedure room initial set up module is further configured to provide virtual image guidance for the medical procedure room set up using the stored one or more technique guides or tutorials.

10. A method for optimizing a medical procedure room initial set up, the method comprising:

obtaining, by a procedure room initial set up module, at least one medical procedure room initial set up input associated with a medical practitioner identifier identifying a medical practitioner, a medical procedure identifier identifying a medical procedure to be performed, and a medical procedure room identifier identifying a medical procedure room for the medical procedure room set up from a storage device;

providing, by the procedure room initial set up module, virtual image guidance via one or more mixed reality devices, for the medical procedure room initial set up based on the received at least one medical procedure room initial set up input;

acquiring, by a procedure input module, data associated with one or more of at least one item, at least one equipment, and at least one personnel in the medical procedure room initial set up via the one or more mixed reality devices;

analyzing, by a machine learning module, prestored data associated with one or more of the at least one item, the at least one equipment, and the at least one personnel in one or more reference medical procedure room initial set ups corresponding to the medical practitioner identified by the medical practitioner identifier performing the medical procedure identified by the medical procedure identifier in the medical procedure room identified by the medical procedure room identifier;

comparing, by the machine learning module, the acquired data associated with one or more of the at least one item, the at least one equipment, and the at least one personnel in the medical procedure room set up with the analyzed prestored data associated with one or more of the at least one item, the at least one equipment, and the at least one personnel in the one or more reference medical procedure room initial set ups;

modifying, by the machine learning module, the at least one medical procedure room initial set up input corresponding to the medical practitioner identifier, the medical procedure identifier, and the medical procedure room identifier for the medical procedure room initial set up based on the comparison, providing, by the machine learning module, the modified at least one medical procedure room initial set up input to the procedure room initial set up module for optimizing the current medical procedure room initial set up, and identifying, by the machine learning module, the modified at least one medical procedure room initial set up input as the at least one medical procedure room initial set up input in the storage device, receiving, by an input module, inputs from one or more medical enabling technologies;

determining, by the machine learning module, data associated with an item or an equipment required in the medical procedure room based on the received inputs, wherein the data includes at least an identifier or a size of the respective item or equipment;

determining, by the machine learning module, whether the acquired data associated with one or more of the item or the equipment in the medical procedure room set up correspond to the determined data associated with the item or the equipment required in the medical procedure room; and providing, by the machine learning module, a recommendation to the procedure room initial set up module to update the virtual image guidance for the medical procedure room set up to include the determined data associated with the item or the equipment, when the acquired data associated with one or more of the item or the equipment in the medical procedure room set up is inconsistent with the determined data associated with the item or the equipment required in the medical procedure room.

11. The method of claim 10, wherein the method further comprises:

comparing, by the machine learning module, the received at least one medical procedure room initial set up input with the acquired data associated with one or more of the at least one item, the at least one equipment, and the at least one personnel in the medical procedure room set up; and generating, by the machine learning module, an alert when the data associated with one or more of the at least one item, the at least one equipment, and the at least one personnel in the medical procedure room set up is inconsistent with the received the at least one medical procedure room set up input.

12. The method of claim 10, wherein the analyzing further comprises determining an optimal relationship of the data associated with one or more of the at least one item, the at least one equipment, and the at least one personnel in the one or more reference medical procedure room initial set ups with the medical practitioner identifier, the medical procedure identifier, and the medical procedure room identifier, and further wherein the comparing comprises determining whether the acquired data associated with one or more of the at least one item, the at least one equipment, and the at least one personnel in the medical procedure room initial set up correspond to the determined optimal relationship for the medical practitioner identifier, the medical procedure identifier, and the medical room identifier.

13. The method of claim 12, wherein the method further comprises: implementing, by the machine learning module, one or more machine learning algorithms to determine the optimal relationship of the data associated with one or more of the at least one item, the at least one equipment, and the at least one personnel in the one or more reference medical procedure room initial set ups with the medical practitioner identifier, the medical procedure identifier, and the medical procedure room identifier.

14. The method of claim 10, further comprising:

providing, by the machine learning module, recommendations to the procedure room initial set up module for optimizing the medical procedure room initial set up based on the comparison; and updating, by the procedure room initial set up module, the virtual image guidance for the medical procedure room initial set up based on the received recommendation.

15. The method of claim 10, wherein the medical procedure room initial set up input includes one or more of a count of at least one disposable item required, a count of at least one chargeable item required, a count of at least one medical device required, a count of at least one primary equipment required, a count of at least one ancillary equipment required, a count of at least one medical personnel required, a geographical positioning of at least one disposable item, a geographical positioning of at least one chargeable item, a geographical positioning of at least one medical device, a geographical positioning of at least one primary equipment, a geographical positioning of at least one ancillary equipment, a geographical positioning of at least one medical personnel, a priority of use of at least one disposable item, a priority of use of at least one chargeable item, a priority of use of at least one medical device, a priority of use of at least one primary equipment, a priority of use of at least one ancillary equipment, an orientation of at least one disposable item, an orientation of at least one chargeable item, an orientation of at least one medical device, an orientation of at least one primary equipment, an orientation of at least one ancillary equipment, and an orientation of at least one medical personnel.

16. The method of claim 10, wherein the data associated with one or more of the at least one item, the at least one equipment, and the at least one personnel in the medical procedure room initial set up include one or more of an orientation and a geographical position of one or more of the at least one item, the at least one equipment, and the at least one personnel in the medical procedure room.

17. The method of claim 10, wherein the data associated with one or more of the at least one item, the at least one equipment, and the at least one personnel in the medical procedure room initial set up include a count of one or more of the at least one item, the at least one equipment, and the at least one personnel in the medical procedure room.

18. The method of claim 10, further comprising:
   storing, by a data module, one or more of technique guides or tutorials associated with the medical procedure room initial set up; and
   providing, by the procedure room initial set up, virtual image guidance for the medical procedure room initial set up using the stored one or more technique guides or tutorials.

* * * * *